US007834244B2

(12) United States Patent
Hu et al.

(10) Patent No.: US 7,834,244 B2
(45) Date of Patent: Nov. 16, 2010

(54) TRANSCRIPTION FACTOR GENE OSNACX FROM RICE AND USE THEREOF FOR IMPROVING PLANT TOLERANCE TO DROUGHT AND SALT

(75) Inventors: Honghong Hu, Wuhan (CN); Lizhong Xiong, Wuhan (CN)

(73) Assignee: Huazhong Agricultural University, Wuhan (CN)

( * ) Notice: Subject to any disclaimer, the term of this patent is extended or adjusted under 35 U.S.C. 154(b) by 116 days.

(21) Appl. No.: 11/722,298

(22) PCT Filed: Dec. 20, 2005

(86) PCT No.: PCT/CN2005/002251

§ 371 (c)(1),
(2), (4) Date: Mar. 11, 2008

(87) PCT Pub. No.: WO2006/066498

PCT Pub. Date: Jun. 29, 2006

(65) Prior Publication Data

US 2008/0263722 A1    Oct. 23, 2008

(51) Int. Cl.
*C12N 15/82* (2006.01)
*A01H 5/00* (2006.01)
(52) U.S. Cl. .................... 800/289; 435/252.3; 435/419; 435/320.1
(58) Field of Classification Search .................. None
See application file for complete search history.

(56) References Cited

U.S. PATENT DOCUMENTS

| | | | |
|---|---|---|---|
| 4,940,838 A | 7/1990 | Schilperoort et al. |
| 4,945,050 A | 7/1990 | Sanford et al. |
| 5,057,422 A | 10/1991 | Bol et al. |
| 5,173,410 A | 12/1992 | Ahlquist |
| 5,187,267 A | 2/1993 | Comai et al. |
| 5,451,513 A | 9/1995 | Maliga et al. |
| 5,500,360 A | 3/1996 | Ahlquist et al. |
| 5,501,967 A | 3/1996 | Offringa et al. |
| 5,545,817 A | 8/1996 | McBride et al. |
| 5,545,818 A | 8/1996 | McBride et al. |
| 5,824,877 A | 10/1998 | Hinchee et al. |
| 5,846,795 A | 12/1998 | Ahlquist et al. |
| 5,866,785 A | 2/1999 | Donson et al. |
| 5,965,794 A | 10/1999 | Turpen |
| 5,977,438 A | 11/1999 | Turpen et al. |
| 5,981,839 A | 11/1999 | Knauf et al. |
| 5,981,840 A | 11/1999 | Zhao et al. |
| 6,051,757 A | 4/2000 | Barton et al. |
| 2004/0019927 A1 | 1/2004 | Sherman et al. |
| 2004/0123343 A1 | 6/2004 | La Rosa et al. |

FOREIGN PATENT DOCUMENTS

| | | |
|---|---|---|
| EP | 0 292 435 | 5/1988 |
| JP | 2004 248638 A | 9/2004 |
| WO | WO 94/13822 | 6/1994 |
| WO | WO 95-16783 | 12/1994 |
| WO | WO 03/000898 A1 | 1/2003 |
| WO | WO 03/000906 * | 1/2003 |
| WO | WO 03/000906 A2 | 1/2003 |

OTHER PUBLICATIONS

GenBank Accession No. AC135594, *Oryza sativa* chromosome 3 BAC OSJNBa0024F18 genomic sequence, complete sequence, Jan. 9, 2004.*
Whisstock J.C. et al. Prediction of protein function from protein sequence and structure. Q Rev Biophys. Aug. 2003;36(3):307-40. Review.*
McCabe, D., et al., "Stable Transformation of Soybean (*Glycine max*) by Particle Acceleration," *Bio/Technology*, 1988, pp. 923-926, vol. 6.
Hinchee, M.., et al., "Production of Transgenic Soybean Plants Using Agrobacterium-Medicated DNA Transfer," *Bio/Technology*, 1988, pp. 915-922, vol. 6.
Koziel, M.., et al., "Field Performance of Elite Transgenic Maize Plants Expressing an Insecticidal Protein Derived from *Bacillus thuringiensis*," *Bio/Technology*, 1993, pp. 194-200, vol. 11.
Datta, S., et al., "Genetically Engineered Fertile IndicaRice Recovered from Protoplasts," *Bio/Technology*, 1990, pp. 736-740, vol. 8.
Christou, P., et al., "Production of Transgenic Rice (*Oryza sativa* L.) Plants from Agronomically Important Indica and Japonic Varieties Via Electric Discharge Particle Acceleration of Exogenous DNA Into Immature Zygotic Embryos,"*Bio/Technology*, 1990, pp. 736-740, vol. 8.
Vasil, V., et al., "Rapid Production of transgenic Wheat Plants by Direct Bombardment of Cultured Immature Embryos," *Bio/Technology*, 1993, pp. 1553-1558, vol. 11.
Sanford J., et al., "Delivery of Substances Into Cells and Tissue using a Particle Bombardment Process," *Particulate Science and Technology*, 1987, pp. 27-37, vol. 5.
Fromm, M., et al., "Inheritance and expression of Chimeric Genes in the Progeny of Transgenic Maize Plants," *Bio/Technology*, 1990, pp. 833-839, vol. 8.
Klein, T.M., et al., "Factors Influencing Gene Delivery Into *Zea mays* Cells by HughVelocity Microprojectiles," *Bio/Technology*, 1988, pp. 559-563, vol. 6.
Somers, D., et al., "Fertile, Transgenic Oat Plants," *Bio/Technology*, 1992, pp. 1589-1594, vol. 10.
Umbeck, P., et al., "Genetically Transformed Cotton (*Gossypium Hirsutum* L.) Plants," *Bio/Technology*, Mar. 1987, pp. 263-266, vol. 5.

(Continued)

*Primary Examiner*—Cynthia Collins
(74) *Attorney, Agent, or Firm*—Alston & Bird LLP

(57) ABSTRACT

The present invention relates to an isolated polynucleotide capable of giving a plant tolerance to drought and/or salt stress, which comprises a polynucleotide sequence as shown in SEQ ID NO:1, and to a promoter capable of giving a plant tolerance to drought and/or salt stress. The present invention also relates to an expression vector comprising the said polynucleotide and/or the said promoter, and to a host cell transformed or transfected by the said expression vector. The present invention further relates to a use of the said polynucleotide or promoter sequence in improvement of plant tolerance to drought and/or salt stress.

8 Claims, 7 Drawing Sheets

OTHER PUBLICATIONS

Proudfoot, N., "Poly(A) Signals,"*Cell*, 1991, pp. 671-674, vol. 64.

Kalderon, D., et al., "A Short Amino Acid Sequence Able to Specify Nuclear Location,"*Cell*, Dec. 1984 (Part 2), pp. 499-509, vol. 39.

Adelman, J., et al., "In Vitro Deletional Mutagenesis for Bacterial Production ofthe 20,000-Dalton Form of Human Pituitary Growth Hormone,"*DNA*, 1983, pp. 183-193, vol. 2.

Crossway, A., et al., "Micromanipulation Techniques in Plants Biotechnology," *BioTechniques*, 1986, pp. 320-334, vol. 4, No. 4.

Fujita, M., et al., "A Dehydration-induced NAC protein, RD26, is involved in a novel ABA- dependent stress-signaling pathway," *The Plant Journal*, 2004, pp. 863-876, vol. 39.

Hiel, Y., et al., "Efficient transformation of rice (*Oryza sativa* L.) mediated by Agrobacterium sequence analysis of the boundaries of the T-DNA," *The Plant Journal*, 1994, pp. 271-282, vol. 6(2).

Nehra, N., et al., "Self-fertile transgenic wheat plans regenerated from isolated scuteller tissues following microprojectile bombardment with two distinct gene constructs," *The Plant Journal*, 1994, pp. 285-297, vol. 5(2).

Koziel, M.., et al., "Transgenic Maize for the Control of European Corn Borer and Other Maize Insect Pests," *Annuals New York Academy of Sciences*, pp. 164-171.

Torbert, K., et al., "Use of paramomycin as a selective agent for oat transformation,"*Plant Cell Reports*, 1995, pp. 635-640, vol. 14.

Svab, Z., et al., "Stable transformation of plastids in higher plants,"*Proc. Natl. Acad. Sci USA*, Nov. 1990, pp. 8526-8530, vol. 87.

Svab, Z.., et al., "High-frequency plastid transformation in tobacco by selection for a chimeric aadA Gene," *Proc. Natl. Acad. Sci USA*, Feb. 1993, pp. 913-917, vol. 90.

Staub, J., et al., "Accumulation of D1 polypeptide in tobacco plastids is regulated via the untranslated region of the pbsA mRNA," *The EMBO Journal*, 1993, pp. 601-606, vol. 12(2).

Staub, J., et al., "Long Regions of Homologous DNA are Incorporated into the Tobacco Plastid Genome by Transformation," *The Plant Cell*, Jan. 1992, pp. 39-45, vol. 4.

Spencer, T.M., et al., "Bialaphos selection of stable transformants from maize cell culture," *Theor Appl Genet*, 1990, pp. 625-631, vol. 79.

Seki, M.., et al., "Monitoring the Expression Pattern of 1300 *Arabidopsis* Genes under Drought and Cold Stresses by Using a Full-Length CDNA Microarray," *The Plant Cell*, Jan. 2001, pp. 61-72, vol. 13.

Schell, J., "Transgenic Plants as Tools to Study the Molecular Organization of Plant Genes," *Science*, pp. 1176-1182, vol. 237.

Sanafacon, H., et al., "A dissection of the cauliflower mosaic virus polyadenylation signal," *Genes & Development*, 1991, pp. 141-149, vol. 5.

Rosenberg, A., et al., "Vectors for selective expression of cloned DNAs by T7 RNA polymerase," *Gene*, 1987, pp. 125-135, vol. 56.

Riggs, C., et al., "Stable transformation of tobacco by electroporation: Evidence for plasmid concatenation," *Proc. Natl. Acad. Sci USA*, Aug. 1986, pp. 5602-5606, vol. 83.

Paszkowski, J., et al., "Direct gene transfer to plants," *The EMBO Journal*, 1984, pp. 2717-2722, vol. 3.

Odell, J.., et al., "Identification of DNA sequences required for activity of the cauliflower mosaic 35S promoter," *Nature*, Feb. 1985, pp. 810-812, vol. 313.

Munroe, D.., et al., "Tales of poly(A): a review,"*Gene*, 1990, pp. 151-158, vol. 91.

Mogen, B., et al., "Upstream Sequences Other than AAUAAA Are required for Efficient Messenger RNA 3'-End Formation in Plants," *The Plant Cell*, Dec. 1990, pp. 1261-1272, vol. 2.

Luehrsen, K., et al., "Intron enhancement of gene expression and the splicing efficiency of introns in maize cells," *Mol Gen Genet*, 1991, pp. 81-93, vol. 225.

Lui, Q., et al., "Two Transcription factors, DREB1 and DREB2, with an EREBP/AP2 DNA Binding Domain Separate Two Cellular Signal Transduction Pathways in Drought and Low-Temperature-responsive Gene Expression, Respectively, in *Arabidopsis*,"*The Plant Cell*, Aug. 1998, pp. 1392-1406, vol. 10.

Lassner, M., et al., "Targeting of T7 RNA polymerase to tobacco nucleimediated by an SV40 nuclear location signal," *Plant Molecular Biology*, 1991, pp. 229-234, vol. 17.

Krens, F.A., et al., "In vitro transformation of plant protoplasts with Ti-plasmid DNA," *Nature*, Mar. 4, 1982, pp. 72-74, vol. 296.

Knudsen, S., et al., "Transformation of the developing barley endosperm, by particle bombardment," *Planta*, 1991, pp. 330-336, vol. 185.

Klein, T., et al., "Transfer of foreign genes into intact maize cells with highvelocity microprojectiles," *Proc. Natl. Acad. Sci USA*, Jun. 1988, pp. 4305-4309, vol. 85.

Klein, T., et al., "Genetic Transformation of Maize Cells by Particle Bombardment,"*Plant Physiol.*, 1989, pp. 440-444, vol. 91.

Kawasaki, S.,et al., "Gene Expression Profiles during the InitialPhase of Salt Stress in Rice," *The Plant Cell*, Apr. 2001, pp. 889-905, vol. 13.

Joshi, C.P., "Putative polyadenylation signals in nuclear genes of higher plants: a compilation and analysis," *Nucleic Acids Research*, 1987, pp. 9627-9640, vol. 15.

Joshi, C.P., "An inspection of the domain between putative TATA box and translation start site in 79 plant genes," *Nucleic Acids Research*, 1987, pp. 6643-6653, vol. 15.

Jahne, A., et al., "Regeneration of transgenic, microspore derived, fertile barley," *Theor Appl Genet*, 1994, pp. 525-533, vol. 89.

Ishida, Y., et al., "High efficiency transformation of maize (*Zea mays* L.) mediated by *Agrobacterium tumefaciens*," *Nature Biotechnology*, Jun. 1996, pp. 745-750, vol. 14.

Hill, M., et al., "Biolistic introduction of a synthetic Bt gene into elite maize,"*Euphytica*, 1995, pp. 119-123, vol. 85.

Hayashimoto, A., et al., "A Polyethylene Glycol-Mediated Protoplast Transformation System for Production of Fertile Transgenic Rice Plants,"*Plant Physiol.*, 1990, pp. 857-863, vol. 93.

Kamm, W., et al., "Transformation of Maize Cells and Regeneration of fertile Transgenic Plants," *The Plant Cell*, Jul. 1990, pp. 603-618, vol. 2.

Fromm, M., et al., "Expression of genes transferred into monocot and dicot plant cellsby electroporation," *Proc. Natl. Acad. Sci.*, Sep. 1985, pp. 5824-5828, vol. 82.

Fraley, R., et al., "Liposome-mediated delivery of tobacco mosaic virus RNA into tobacco protoplasts: A sensitive assay for monitoring liposomeprotoplast interactions," *Proc. Natl. Acad. Sci. USA*, Mar. 1982, pp. 1859-1863, vol. 79.

Crossway, A., et al., "Integration of foreign DNA following microinjection of tobacco mesophyll protoplasts," *Mol Gen Genet.*, 1986, pp. 179-185, vol. 202.

Chao, W., et al., "Leucine Aminopeptidase RNAs, Proteins, and Activities Increase in Response to Water Deficit, Salinity, and the Wound Signals Systemin, Methyl Jasmonate, and Abscisic Acid," *Plant Physiology*, Aug. 1999, pp. 979-992, vol. 120.

Casas, A., et al., "Transgenic sorghum plants via microprojectile bombardment," *Proc. Natl. Acad. Sci. USA*, Dec. 1993, pp. 11212-11216, vol. 90.

Carpita, N., et al., "Chemical Structure of the Cell Walls of Dwarf maize and Changes Mediated by Gibberellin," *Plant Physiol.*, 1988, pp. 671-678, vol. 88.

Bourouis, M., et al., "Vectors containing a prokaryotic dihydrofolate reductase gene transform *Drosophila* cells to," *The EMBO Journal*, 1983, pp. 1099-1104, vol. 2(7).

Blochlinger, K., et al., "Hygromycin B Phosphotransferase as a Selectable marker for DNA Transfer Experiments with Higher Eucaryotic Cells" *Molecular and Cellular Biology*, Dec. 1984, pp. 2929-2931, vol. 4(12).

Bevan, M., et al., "A chimaeric antibiotic resistance gene as a selectable marker for plant cell transformation," *Nature*, Jul. 1983, pp. 184-187, vol. 82.

Beachy, R., et al., "Accumulation and assembly of soybean B-conglycinin in seeds of transformed petunia plants," *The EMBO Journal*, 1985, pp. 3047-3053, vol. 4(12).

Ballas, N., et al., "Efficient functioning of plant promoters and poly(A) sites in *Xenopus oocytes*," *Nucleic Acids Research.*, 1989, pp. 7891-7903, vol. 17(19).

Xiong, L., et al., "Cell Signaling during Cold, Drought, and Salt Stress" *The Plant Cell*, 2002, pp. S165-S183.

White, J., et al., "A cassette containing the bar gene of *Streptomyces hygroscopicus*: a selectable marker for plant transformation," *Nucleic Acids Research*, 1989, pp. 1062, vol. 18(4).

Weising, K., et al., "Foreign Genes in the Plants: Transfer, Structure, Expression, and Applications," *Annu. Rev. Genet.*, 1988, pp. 421-479, vol. 22.

Weeks, J., et al., "Rapid Production of Multiple Independent Lines of fertile Transgenic Wheat (*Triticum aestivum*)," *Plant Physiol.*, 1993, pp. 1077-1084, vol. 102.

Wan, Y, et al., "Generation of Large Numbers of Independently Transformed Fertile Barley Plants," *Plant Physiol.*, 1994, pp. 37-48, vol. 104.

Vieira, J., et al., "Expression of genes transferred into monocot and dicot plant cells by electroporation," *Proc. Natl. Acad. Sci.*, Sep. 1985, pp. 5824-5828, vol. 82.

Vieira, J., et al., "The pUC plansimids, an M13mp7-derived system for insertion mutagenesis and sequencing with synthetic universal primers," *Gene*, 1982, pp. 259-268, vol. 19.

Guerineau, F., et al., "Effect of deletions in the cauliflower mosaic virus polyadenylation sequence on the choice of the polyadenylation sites in tobacco protoplasts" *Mol Gen Genet*, 1991, pp. 141-144, vol. 226.

Genbank Report for Accession AK067690, Oct. 7, 2003.

International Search Report completed Feb. 16, 2006, PCT/CN2005/00225.

Fujita, M., et al., "A Dehydration-Induced NAC Protein, RD26, is Involved in a Novel ABA-Dependent Stress-Signaling Pathway", *The Plant Journal*, (2004), 39:863-876.

* cited by examiner

US 7,834,244 B2

TRANSCRIPTION FACTOR GENE OSNACX FROM RICE AND USE THEREOF FOR IMPROVING PLANT TOLERANCE TO DROUGHT AND SALT

TECHNICAL FIELD

The present invention relates to an isolated polynucleotide capable of giving a plant tolerance to drought and/or salt stress, which comprises a polynucleotide sequence as shown in SEQ ID NO:1, and to a promoter capable of giving a plant tolerance to drought and/or salt stress. The present invention also relates to an expression vector comprising the said polynucleotide and/or the said promoter, and to a host cell transformed or transfected by the said expression vector. The present invention further relates to a use of the said polynucleotide or promoter sequence in improvement of plant tolerance to drought and/or salt stress.

BACKGROUND ART

The growth of plants usually are influenced by many environmental factors, wherein drought and/or salt damage are main factors resulting in great reduction of crop production in many areas. Thus, it always a major aim to develop crop species with stress tolerance in researches of agricultural science and technology.

For resisting or adapting to disadvantageous environmental factors, plants receive extracellular changes of environmental conditions and transfer them through many pathways into cells to induce expressions of some responding genes and generate some functional proteins, osmoregulation substances as well as transcription factors for signal transmission and gene expression regulation so that plants are able to make corresponding responses to environmental changes and avoid damages caused by drought, high salt and/or low temperature stresses. (Xiong et al, Cell signaling during cold, drought and salt stress. Plant Cell. 14 (suppl), S165-S183, 2002). The regulating factors finely regulate the expression of functional genes for responding environmental changes. When plants encounter stresses, transcription factor as a controlling gene is able to regulate the expression of a series of downstream genes to enhance the tolerance of plants to the stresses.

Kawasaki et al (2001) utilized microarrays to analyze the early expression profile of rice under high salt stress, and disclosed that a great number of genes were induced or inhibited and the induction and expression of these genes were regulated by transcription factor (Kawasaki S, Borchert C, Deyholos M, Wang H, Brazille S, Kawai K, Galbraith D and Bohnert H J. Gene expression profiles during the initial phase of salt stress in rice, Plant Cell, 2001, 13: 889-905). It is found that transcription factor families of AP2/EREBP, Zinc finger, Myb, bZIP in *Arabidopsis thaliana* are induced to be expressed or inhibited under different stresses (Shinozaki K et al, Monitoring the Expression Pattern of 1300 *Arabidopsis* Genes under Drought and Cold Stresses by Using a Full-Length cDNA Microarray, Plant Cell, 2001, 13: 61-72). Thus, it is deemed that these transcription families are very important in regulation during the procedure of plant response to stresses. Therefore, the separation and identification of transcription factors having core regulation function for response to stresses and the use thereof for genetic improvement of crop to resist stresses are important and meaningful for seed breeding.

Based on the known information of *Arabidopsis thaliana* transcription factors, some studies have been done to improve plant tolerances. Transgenic *Arabidopsis thaliana* plants cultured by using EREB1A and DREB2A have higher tolerances to low temperature, drought and high salinitiy than the wild type (Liu Q et al, Two transcription factors, DREB1 and DREB2, with an EREBP/AP2 DNA domains separate two cellular signal thansduction pathways in drought—and low-temperature-responsive gene expression, respectively, in *Arabidopsis*. Plant Cell. 1998, 10: 1391-1406). The research group of Thomashow M F in Michigan State University (U.S.A.) also cultured plants with enhanced freezing tolerance by using *Arabidopsis thaliana* CBF1 gene in genetic transformation.

Rice is one of the most important alimentary corps. The tolerance to drought and/or salt is particularly important for rice. However, no transgenic rice plant with tolerance to drought and/or salt has been developed so far. Thus, it is meaningful and important to find out transcription factor associated with tolerance to drought and/or salt for culturing a rice plant with tolerance to drought and/or freezing and thereby increasing rich production.

SUMMARY OF THE INVENTION

One object of the present invention is to provide an isolated polynucleotide capable of giving a plant, preferably rice, tolerance to drought and/or salt stress, which comprises a nucleotide sequence as shown in SEQ ID NO:1, or a conservative variant or degenerate sequence comprising one or more substitutions, deletions, additions and/or insertions in the said nucleotide sequence, or a sequence hybridizable with the said sequence under moderate stringent condition, or a complementary sequence thereof, or a variant or derivative having at least 95% homology and same or similar biological function to the said nucleotide sequence.

In one embodiment of the present invention, the said polynucleotide consists of the DNA sequence as shown in SEQ ID NO:1. In another embodiment of the present invention, the said polynucleotide consists of the DNA sequence as shown in the positions 1374-2453 of SEQ ID NO:1.

Another object of the present invention is to provide a promoter capable of giving a plant, preferably rice, tolerance to drought and salt stress, which comprises a nucleotide sequence as shown in the DNA sequence of the positions 1-1373 of SEQ ID NO:1, or a conservative variant or degenerate sequence comprising one or more substitutions, deletions, additions and/or insertions into the said nucleotide sequence, or a sequence hybridizable with the said sequence under moderate stringent condition, or a complementary sequence thereof, or a variant or derivative having at least 95% homology and same or similar biological function to the said nucleotide sequence. In one embodiment of the present invention, the said promoter consists of the DNA sequence as shown in the DNA sequence of the positions 1-1373 of SEQ ID NO:1.

Another object of the present invention is to provide an expression vector comprising the said polynucleotide sequence and/or the said promoter sequence.

Another object of the present invention is to provide a host cell transformed or transfected by the said expression vector.

Another object of the present invention is to provide a use of the said polynucleotide sequence and/or the said promoter for increasing tolerance to drought and/or salt stress in plant, preferably rice.

DETAILED DESCRIPTION OF THE INVENTION

The object of the present invention is to isolate a DNA fragment comprising transcription factor gene complete encoding region, to clone it, and to use it for improvement of tolerance of rice or other plants to drought. The present invention is based on the discovery by structure analysis of the obtained gene that belongs to plant-specific transcription factor NAC family, and thus the said transcription factor is named as OsNACx.

In the present invention, the term "isolated polynucleotide capable of giving a plant tolerance to drought and/or salt stress" represents the polynucleotide sequence as shown in SEQ ID NO:1, and further comprises all variants or derivatives having at least 95% homology and same or similar biological function to the sequence as shown in SEQ ID NO:1.

The term "isolated" means "artificially" changed from natural status and/or isolated from natural environment. Thus, if an "isolated" component or substance existing in nature is "isolated", it has been changed or removed from its initial environment or been subject to both. For example, a polynucleotide or polypeptide naturally existing in live animal is not "isolated", but the same polynucleotide or polypeptide isolated from its natural status is "isolated", which is exactly the term used herein.

The term "polynucleotide(s)", as used herein, means a single or double stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (DNA, 2: 183, 1983). Nucleotide variants may be naturally occurring allelic variants, or non-naturally occurring variants. Variant nucleotide sequences preferably exhibit at least about 70%, more preferably at least about 80% and most preferably at least about 90% homology (determined as described below) to the recited sequence.

The term "homology" when used in relation to nucleic acids refers to a degree of complementarity. There may be partial homology or complete homology (in other words, identity). "Sequence identity" refers to a measure of relatedness between two or more nucleic acids, and is given as a percentage with reference to the total comparison length. The identity calculation takes into account those nucleotide residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid is referred to using the functional term "substantially homologous". The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (in other words, the hybridization) of a sequence which is completely homologous to a target under conditions of low stringency. This is not to say that conditions of low stringency are such that non-specific binding is permitted; low stringency conditions require that the binding of two sequences to one another be a specific (in other words, selective) interaction. The absence of non-specific binding may be tested by the use of a second target which lacks even a partial degree of complementarity (for example, less than about 30% identity); in the absence of non-specific binding the probe will not hybridize to the second non-complementary target.

When used in reference to a double-stranded nucleic acid sequence such as acDNA or genomic clone, the term "substantially homologous" refers to any probe which can hybridize to either or both strands of the double-stranded nucleic acid sequence under conditions of low stringency as described in.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4 \times H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4 \times H_2O$ and 1.85 g/l EDTA, pH adjusted to 7.4 with NaOH), 0.5% SDS, 5×Denhardt's reagent and 100: g/ml denatured salmon sperm DNA followed by washing in a solution comprising 0.1×SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (for example, the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (for example, increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low to high stringency as described above.

When used in reference to a single-stranded nucleic acid sequence, the term "substantially homologous" refers to any probe that can hybridize (in other words, it is the complement of) the single-stranded nucleic acid sequence under conditions of low to high stringency as described above.

The term "hybridization" refers to the pairing of complementary nucleic acids. Hybridization and the strength of hybridization (in other words, the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized".

The term "$T_m$" refers to the "melting temperature" of a nucleic acid. The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41$ (% G+C), when a nucleic acid is in aqueous solution at 1M NaCl (See for example, Anderson and Young, Quantitative Filter Hybridization (1985) in Nucleic Acid Hybridization). Other references include more sophisticated computations that take structural as well as sequence characteristics into account for the calculation of $T_m$.

As used herein the term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

Preferably, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity. In general, all or a portion of polynucleotides described herein may be prepared using any of several techniques.

In other words, for obtaining a polynucleotide with a nucleotide sequence having at least 95% identity to the reference nucleotide sequence, up to 5% nucleotides in the reference sequence could be deleted or substituted by other nucleotides; or up to 5% nucleotides with reference to the total nucleotides of the reference sequence could be inserted into the reference sequence; or up to 5% nucleotides with reference to the total nucleotides of the reference sequence could be subject to a combination of deletion, insertion and substitution. These mutations in the reference sequence could occur at 5- or 3-terminal position of the reference nucleotide sequence or at any position between these terminal positions, and they exist in the reference nucleotide sequence either in individual manner or in one or more adjacent groups.

One aspect of the present invention relates to an isolated polynucleotide capable of giving a plant tolerance to drought and/or salt stress, which comprises a nucleotide sequence as shown in SEQ ID NO:1, or a conservative variant or degenerate sequence comprising one or more substitutions, deletions, additions and/or insertions into the said nucleotide sequence, or a sequence hybridizable with the said sequence under moderate stringent condition, or a complementary sequence thereof, or a variant or derivative having at least 95% homology and same or similar biological function to the said nucleotide sequence.

In one embodiment of the present invention, the said polynucleotide consists of the DNA sequence as shown in SEQ ID NO:1. In another embodiment of the present invention, the said polynucleotide consists of the DNA sequence as shown in the positions 1374-2453 of SEQ ID NO:1.

Another aspect of the present invention relates to a promoter capable of giving a plant, preferably rice, tolerance to drought and salt stress, which comprises a nucleotide sequence as shown in the DNA sequence of the positions 1-1373 of SEQ ID NO:1, or a conservative variant or degenerate sequence comprising one or more substitution, deletion, addition and/or insertion in the said nucleotide sequence, or a sequence hybridizable with the said sequence under moderate stringent condition, or a complementary sequence thereof, or a variant or derivative having at least 95% homology and same or similar biological function to the said nucleotide sequence. In one embodiment of the present invention, the said promoter consists of the DNA sequence as shown in the DNA sequence of the positions 1-1373 of SEQ ID NO:1.

The gene or homologous gene of the present invention is able to be screened from cDNA and genomic library by using a polynucleotide-specific oligonucleotide primer/probe such as the cloned OsNACx gene. Similarly, the OsNACx gene of the present invention and any DNA fragment of interest or DNA fragment homologous to it can also be obtained from amplification of genome, mRNA and cDNA by using PCR (polymerase chain reaction) technology. A sequence comprising OsNACx gene can be isolated and obtained by using the above techniques, and a transgenic plant with enhanced tolerance to drought and salt stress can be obtained by transforming a plant with the said sequence and any expression vector capable of inducing the expression of an exogenous gene in the plant.

For example, polymerase chain reaction can be used for amplifying the sequence from cDNA, wherein the said cDNA is prepared from the isolated RNA. A sequence-specific primer for this amplification can be designed based on the sequence as shown in SEQ ID NO:1, or can be purchased or synthesized. Then, the PCR product can be separated by gel electrophoresis and detected by methods well known by those skilled technicians in the art.

The term "polynucleotide molecule-specific oligonucleotide primer/probe" refers to an oligonucleotide sequence having at least 80%, preferably at least 90%, more preferably at least 95% identity to the desired polynucleotide, or to an anti-sence oligonucleotide of a sequence that has at least 80%, preferably 90%, more preferably 95% identity to the desired polynucleotide.

The very useful oligonucleotide primer and/or probe in the present invention has at least 10-40 nucleotides. In one preferable embodiment, the oligonucleotide primer includes at least about 10 consecutive nucleotides of the said polynucleotide. Preferably, the oligonucleotide used in the present invention includes at least about 15 consecutive nucleotides of the said polynucleotide. The technologies based on PCR test and hybridization in situ test are well known in the art.

Another aspect of the present invention relates to an expression vector comprising the said polynucleotide sequence and/or the said promoter sequence. When the gene of the present invention is constructed into a plant expression vector, any strong promoter or inducible promoter can be added before its starting nucleotide for transcription. When the gene of the present invention is constructed into a plant expression vector, enhancers can also be used, and these enhancer regions can be ATG initiation codons, adjacent region initiation codons, etc., but must be identical to the reading frame of the encoding sequence in order to ensure the translation of whole sequence.

The expression vector carrying the polynucleotide sequence of the OsNACx gene of the present invention can be introduced into plant cells by conventional biological methods such as Ti plasmid, plant virus vector, direct DNA transformation, microinjection, electroporation and the like (Weissbach, 1998, Method for Plant Molecular Biology VIII, Academy Press, New York, pp. 411-463; Geiserson and Corey, 1998, Plant Molecular Biology (2$^{nd}$ Edition).

The plants of the present invention include but are not limited to: tomato, potato, tobacco, pepper, rice, corn, barley, wheat, *Brassica*, *Arabidopsis*, sunflower, soybean, poplar, and pine. Preferred plant is rice, also includes non-agronomic species which are useful in developing appropriate expression vectors such as tobacco, rapid cycling *Brassica* species, and *Arabidopsis thaliana*.

Methods which are well known to those skilled in the art may be used to construct expression vectors containing a heterologous gene and appropriate transcriptional and translational control elements. These methods include in vitro recombinant DNA techniques, synthetic techniques, and in vivo genetic recombination. Such techniques are widely described in the art (See for example, Sambrook. et al (1989), Molecular Cloning, A Laboratory Manual, Cold Spring Harbor Press, Plainview, N.Y., and Ausubel, F. M., et al (1989), Current Protocols in Molecular Biology, John Wiley & Sons, New York, N.Y.).

In general, these vectors comprise the polynucleotide sequence of the invention (as described above) operably linked to a promoter and other regulatory sequences (for example, enhancers, polyadenylation signals, etc.) required for expression in a plant.

Promoters used in the present invention include but are not limited to constitutive promoters, tissue-, organ-, and developmentally-specific promoters, and inducible promoters. Examples of promoters include but are not limited to: constitutive promoter 35S of cauliflower mosaic virus; a wound-inducible promoter from tomato, leucine amino peptidase ("LAP", Chao et al. (1999), Plant Physiol 120: 979-992); a chemically-inducible promoter from tobacco, Pathogenesis-Related 1 (PR1) (induced by salicylic acid and BTH (benzothiadiazole-7-carbothioic acid S-methyl ester)); a tomato proteinase inhibitor II promoter (PIN2) or LAP promoter (both inducible with methyl jasmonate); a heat shock promoter (U.S. Pat. No. 5,187,267); a tetracycline-inducible promoter (U.S. Pat. No. 5,057,422); and seed-specific promoters, such as those for seed storage proteins (for example, phaseolin, napin, oleosin, and a promoter for soybean beta conglycin (Beachy et al. (1985), EMBO J. 4: 3047-3053)). All references cited herein are incorporated in their entirety.

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters of the present invention. Transcriptional terminators are responsible for the termination of transcription beyond the transcript and its correct polyadenylation. Appropriate transcriptional terminators and those which are known to function in plants include, but are not limited to, the CaMV35S terminator, the tml terminator, the pea rbcS E9 terminator, and the nopaline and octopine synthase terminator (See for example, Odell et al. (1985) Nature 313:810; Rosenberg et al. (1987) Gene, 56: 125; Guerineau et al. (1991) Mol. Gen. Genet., 262: 141; Proudfoot (1991) Cell, 64: 671; Sanfacon et al. Genes Dev., 5: 141; Mogen et al. (1990) Plant Cell, 2: 1261; Munroe et al (1990) Gene, 91: 151; Ballad et al. (1989) Nucleic Acids Res. 17: 7891; Joshi et al. (1987) Nucleic Acid Res., 15: 9627).

In some embodiments of the present invention, the construct for expression of the nucleic acid sequence of interest also includes a regulator such as a nuclear localization signal (Calderone et al. (1984) Cell 39: 499; Lassoer et al. (1991) Plant Molecular Biology 17: 229), a plant translational consensus sequence (Joshi (1987) Nucleic Acids Research 15: 6643), an intron (Luehrsen and Walbot (1991) Mol. Gen. Genet. 225:81), and the like, operably linked to the nucleic acid sequence encoding plant CPA-FAS.

In preparing the construct comprising a nucleic acid sequence encoding plant CPA-FAS, various DNA fragments can be manipulated, so as to provide for the DNA sequences in the desired orientation (for example, sense or antisense) orientation and, as appropriate, in the desired reading frame. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (for example, transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (Messing and Vierra (1982) Gene 19: 259; Bevan et al. (1983) Nature 304: 184), the bar gene which confers resistance to the herbicide phosphinothricin (White et al. (1990) Nucl Acids Res. 18: 1062; Spencer et al. (1990) Theor. Appl. Genet. 79: 625), the hph gene which confers resistance to the antibiotic hygromycin (Blochlinger and Diggelmann (1984) Mol. Cell. Biol. 4: 2929), and the dhfr gene, which confers resistance to methotrexate (Bourouis et al. (1983) EMBO J., 2: 1099).

In some preferred embodiments, the vector is adapted for use in an *Agrobacterium* mediated transfection process (See for example, U.S. Pat. Nos. 5,981,839; 6,051,757; 5,981,840; 5,824,877; and 4,940,838; all of which are incorporated herein by reference). Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJI shuttle vector and the non-oncogenic Ti plasmid pGV3850. The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available.

In other embodiments of the invention, the nucleic acid sequence of interest is targeted to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (U.S. Pat. No. 5,501,967). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

In yet other embodiments, the nucleic acids of the present invention is utilized to construct vectors derived from plant (+) RNA viruses (for example, brome mosaic virus, tobacco mosaic virus, alfalfa mosaic virus, cucumber mosaic virus, tomato mosaic virus, and combinations and hybrids thereof). Methods for the construction and use of such viruses are described in U.S. Pat. Nos. 5,846,795; 5,500,360; 5,173,410; 5,965,794; 5,977,438; and 5,866,785, all of which are incorporated herein by reference.

Those skilled in the art will appreciate that the choice of method might depend on the type of plant targeted for transformation. In some embodiments, the vector is maintained episomally. In other embodiments, the vector is integrated into the genome.

In some embodiments, direct transformation in the plastid genome is used to introduce the vector into the plant cell (See for example, U.S. Pat. Nos. 5,451,513; 5,545,817; 5,545,818; PCT application WO95/16783). The basic technique for chloroplast transformation involves introducing regions of cloned plastid DNA flanking a selectable marker together with the nucleic acid encoding the RNA sequences of interest into a suitable target tissue (for example, using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab et al (1990) PNAS, 87: 8526; Staub and Maliga, (1992) Plant Cell, 4: 39). The presence of cloning sites between these markers allowed creation of a plastid targeting vector introduction of foreign DNA molecules (Staub and Maliga (1993) EMBO J., 12:601). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga (1993) PNAS, 90: 913). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAs encoded by the DNA molecule.

In other embodiments, vectors useful in the practice of the present invention are microinjected directly into plant cells by use of micropipettes to mechanically transfer the recombinant DNA (Crossway (1985) Mol. Gen. Genet, 202: 179). In still other embodiments, the vector is transferred into the plant cell by using polyethylene glycol (Krens et al. (1982) Nature, 296: 72; Crossway et al. (1986) BioTechniques, 4: 320); fusion of protoplasts with other entities, either minicells, cells, lysosomes or other fusible lipid-surfaced bodies (Fraley et al. (1982) Proc. Natl. Acad. Sci., USA, 79: 1859); protoplast transformation (EP 0 292 435); direct gene transfer (Paszkowski et al. (1984) EMBO J., 3: 2717; Hayashimoto et al (1990) Plant Physiol. 93: 857).

In still further embodiments, the vector may also be introduced into the plant cells by electroporation. (Fromm, et al. (1985) Pro. Natl Acad. Sci. USA 82: 5824; Riggs et al. (1986) Proc. Natl. Acad. Sci. USA 83:5602). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In yet other embodiments, the vector is introduced through ballistic particle acceleration using devices (for example, available from Agracetus, Inc., Madison, Wis. and Dupont, Inc., Wilmington, Del.) (See for example, U.S. Pat. No. 4,945, 050; and McCabe et al. (1988) Biotechnology 6: 923). See also, Weissinger et al. (1988) Annual Rev. Genet. 22:421; Sanford et al. (1987) Particulate Science and Technology, 5:27 (onion); Svab et al. (1990) Proc. Natl. Acad. Sci. USA, 87:8526 (tobacco chloroplast); Christou et al. (1988) Plant Physiol., 87:671 (soybean); McCabe et al. (1988) Bio/Technology 6:923 (soybean); Klein et al. (1988) Proc. Natl. Acad. Sci. USA, 85:4305 (maize); Klein et al. (1988) Bio/Technology, 6:559 (maize); Klein et al. (1988) Plant Physiol., 91:4404 (maize); Fromm et al. (1990) Bio/Technology, 8: 833; and Gordon-Kamm et al. (1990) Plant Cell, 2:603 (maize); Koziel et al. (1993) Biotechnology, 11:194 (maize); Hill et al. (1995) Euphytica, 85:119 and Koziel et al. (1996) Annals of the New York Academy of Sciences 792:164; Shimamoto et al. (1989) Nature 338:274 (rice); Christou et al. (1991) Biotechnology, 9:957 (rice); Datta et al. (1990) Bio/Technology 8:736 (rice); European Patent Application EP0, 332,581 (orchardgrass and other Pooideae); Vasil et al. (1993) Biotechnology, 11:1553 (wheat); Weeks et al. (1993) Plant Physiol., 102:1077 (wheat); Wan et al. (1994) Plant Physiol. 104:37 (barley); Jahne et al. (1994) Theor. Appl. Genet. 89:525 (barley); Knudsen and Muller (1991) Planta, 185:330 (barley); Umbeck et al. (1987) Bio/Technology 5:263 (cotton); Casas et al (1993) Proc. Natl. Acad. Sci. USA 90:11212 (sorghum); Somers et al. (1992) Bio/Technology 10:1589 (oat); Torbert et al. (1995) Plant Cell Reports, 14:635 (oat); Weeks et al. (1993) Plant Physiol., 102:1077 (wheat); Chang et al., WO 94/13822 (wheat); and Nehra et al. (1994) The Plant Journal, 5: 285 (wheat).

In addition to direct transformation, in some embodiments, the vectors comprising a nucleic acid sequence encoding a plant CPA-FAS of the present invention are transferred using *Agrobacterium*-mediated transformation (Hinchee et al. (1988) Biotechnology, 6:915; Ishida et al. (1996) Nature Biotechnology 14:745). *Agrobacterium* is a representative genus of the gram-negative Rhizomaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (for example, nucleic acid sequences operatively linked to a promoter of the present invention), can be introduced into appropriate plant cells, by means of the Ti plasmid of *Agrobacterium tumefaciens*. The Ti plasmid is transmitted to plant cells on infection by *Agrobacterium tumefaciens*, and is stably integrated into the plant genome (Schell (1987) Science, 237:1176). Species which are susceptible infection by *Agrobacterium* may be transformed in vitro. Alternatively, plants may be transformed in vivo, such as by transformation of a whole plant by *Agrobacteria* infiltration of adult plants, as in a "floral dip" method (Bechtold N, Ellis J, Pelletier G (1993) Cr. Acad. Sci. III-Vie 316:1194-1199).

Another aspect of the present invention relates to a host cell transformed or transfected by the above said expression vector. The hosts that can be transformed by an expression vector comprising the OsNACx gene of the present invention include but are not limited to tomato, potato, tobacco, pepper, rice, corn, barley, wheat, *Brassica, Arabidopsis*, sunflower, soybean, poplar, and pine, preferable rice.

Another aspect of the present invention relates to use of the above said polynucleotide sequence and/or promoter sequence for enhancing plant tolerance to drought and/or salt stress. The plants of the present invention include but are not limited to tomato, potato, tobacco, pepper, rice, corn, barley, wheat, *Brassica, Arabidopsis*, sunflower, soybean, poplar, and pine, preferably rice.

In one embodiment of the present invention, the expression of the said promoter sequence is stress inducible expression, so that the said promoter is an inducible promoter. When the promoter fragment of the present invention and any gene of interest are simultaneously linked in an appropriate expression vector and used to transform a plant host, the stress inducible expression of the gene of interest enhances the tolerance of plant to stress.

BRIEF DESCRIPTION OF THE DRAWING

SEQ ID NO:1 in the sequence listing shows the DNA fragment sequence which is isolated and cloned in the present invention and comprises an OsNACx gene encoding region and a promoter region.

In FIG. 3: Gn represents gene number; Ex represents exon; Init represents gene initiation exon; Term represents gene termination exon; Prom represents fundamental promoter; PlyA represents PolyA; S represents DNA chain, wherein "+" represents the DNA sequence chain which is inputted during the analysis process; Begin represents the initiation position of exon, promotor or polyA in the inputted DNA sequence; End represents the termination position of exon, promotor or polyA in the inputted DNA sequence; Len represents the sequence length (bp) of exon, promotor or polyA; Fr represents the translation reading frame (3 translation reading frames per DNA sequence); I/Ac represents the 3' splice site score; Do/t represents the 5' splice site score; CodRg represents the translation region score; P represents the exon probability; Tscr represents the exon score.

FIG. 8A shows the expression of OsNACx-GFP in resistance callus detected by fluorescence microscope; FIG. 8B shows the subcellular localization of OsNACx-GFP in callus cells, wherein (a) is the callus section dyed by fluorochrome propidium iodide, (b) is the expression image of GFP under green fluorescence, (c) is the synthetical result of red and green fluorescences.

EXAMPLES

During the initial research period of the present invention, the cDNA clone 04I24 of the rice variety MingHui 63 (a rice variety which is widely extended in China). The said cDNA is the cDNA fragment of OsNACx gene. The inventors of the present invention found that it is a new stress-associated regulation gene.

Figures 2, 3:
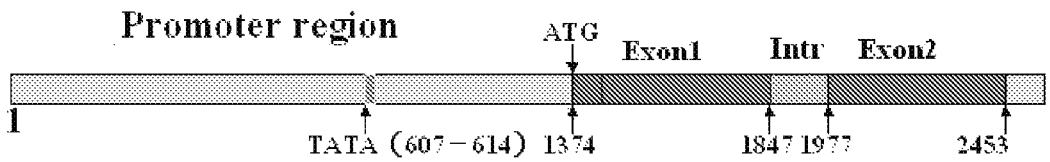
FIG. 2: The result of homology comparison between OsNACx gene (SEQ ID NO:2) and NAC transcription factors (e.g., OsNAC3 (SEQ ID NO:3); OsNAC4 (SEQ ID NO:4); OsNAC6 (SEQ ID NO:5); RD26 (SEQ ID NO:6); and AtNAC1 (SEQ ID NO:7)) using ClustalW software (a public software).
FIG. 3: The result of analysis on the integrate OsNACx gene sequence by GENSCAN gene structure forecasting software (see on the World Wide Web at genes.mit.edu/GENSCAN).
Figure 4:
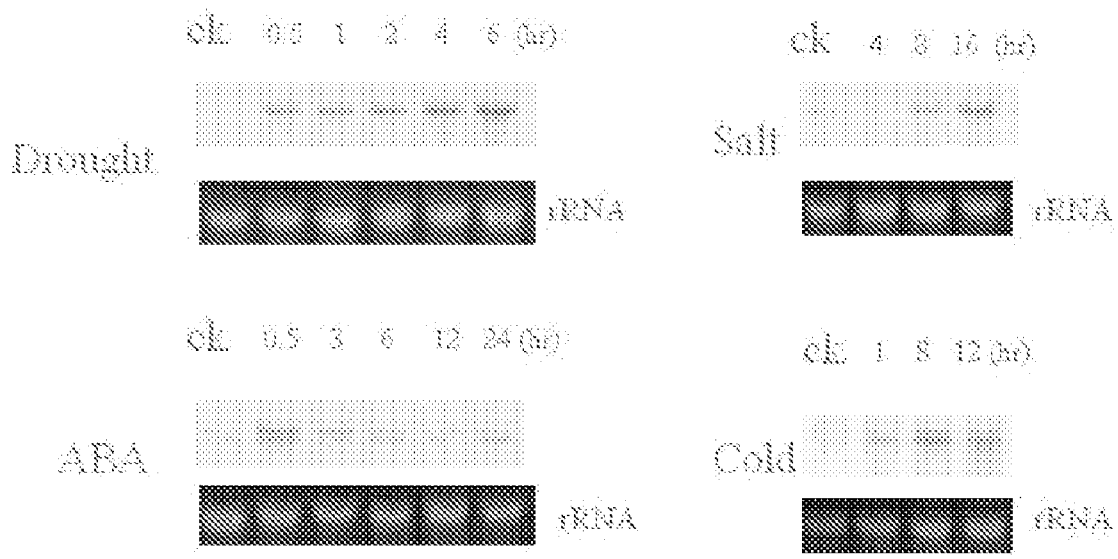
FIG. 4: The OsNACx gene expression levels detected by Northern hybridization assay at different time points under stresses such as drought, high-salinity, low temperature and ABA, etc.
Figure 6:
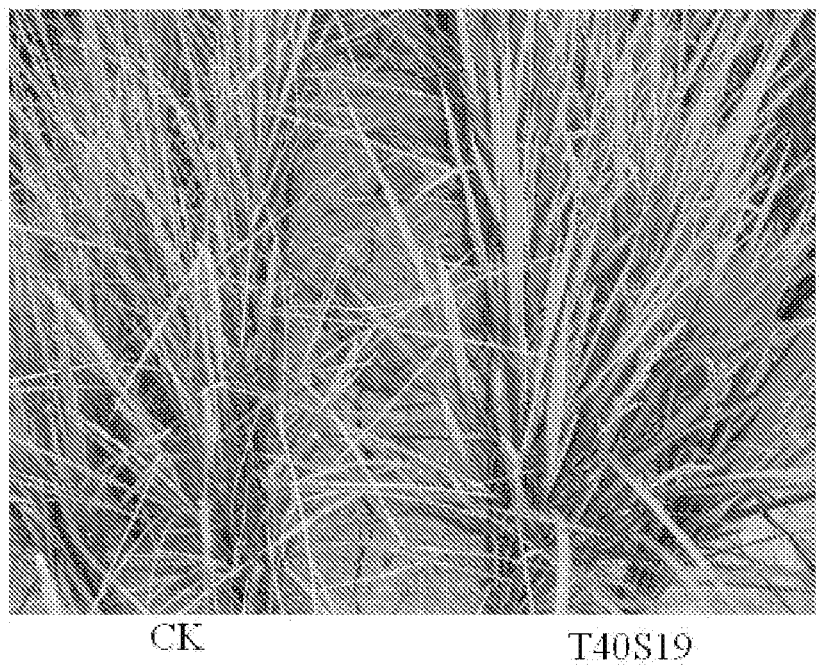
FIG. 6: The growth of transgenic families with overexpression of OsNACx during adult stage after 22 days of drought stress in field.
Figure 7:
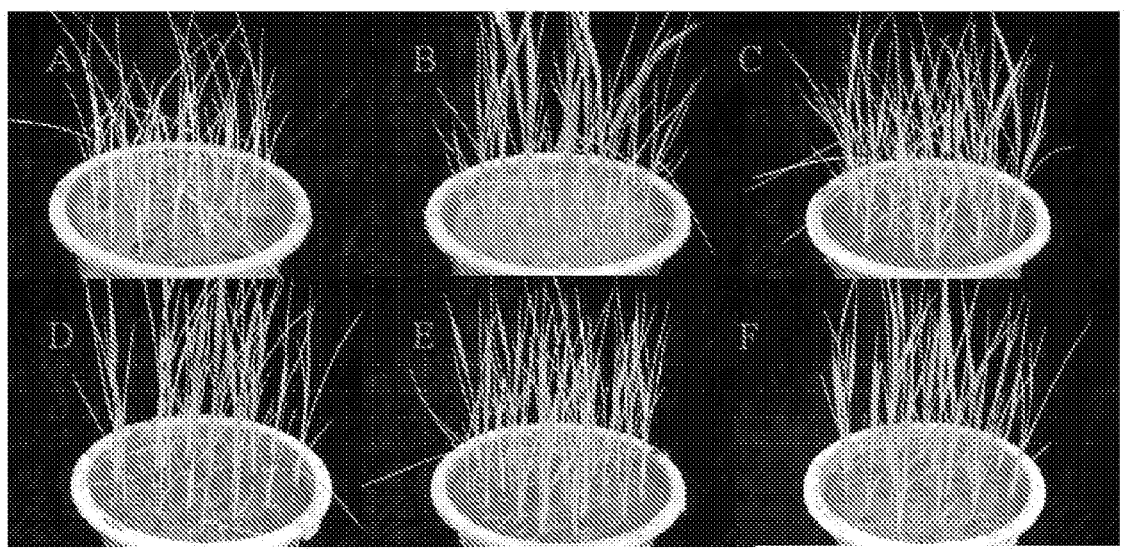
FIG. 7: The growth of transgenic families with overexpression of OsNACx during seedling stage after 12 days of high salinity (200 mM) stress, wherein A represents the control, B represents the transgenic family T40S19, C represents the transgenic family T40S24, D represents the transgenic family T40S26, E represents the transgenic family T40S8, and F represents the transgenic family T40S25.

Specifically, (1) it was found by cDNA chip technique that the expression amount of the said cDNA clone 04I24 in the rice variety "Zhonghan No. 5" (a rice variety which was provided by Shanghai Agriculture Academy of China and was publically used in China) increased 3.5 times after drought stress treatment for 15 days. The results of sequencing and analysis indicated that the product encoded thereby was up to 64% homologous with OsNAC4 (FIG. 2). Due to the significant difference of expression amount before and after drought treatment and the functional characteristics of the clone, it is deemed that the gene of clone 04I24 participated in the expression of regulation gene under drought stress; (2) according to the analysis of expression profile of the said gene under stress (see FIG. 4), it is found that the expression of said gene increased significantly; and (3) the transgenic plant with overexpression of the intact gene exhibited a significantly enhanced tolerance to drought and high-salinity (FIG. 6 and FIG. 7).

The above results show that OsNACx gene is a stress-associated regulation gene and participates in the regulation of tolerance not only to drought but also high-salinity and coldness.

Figure 1:
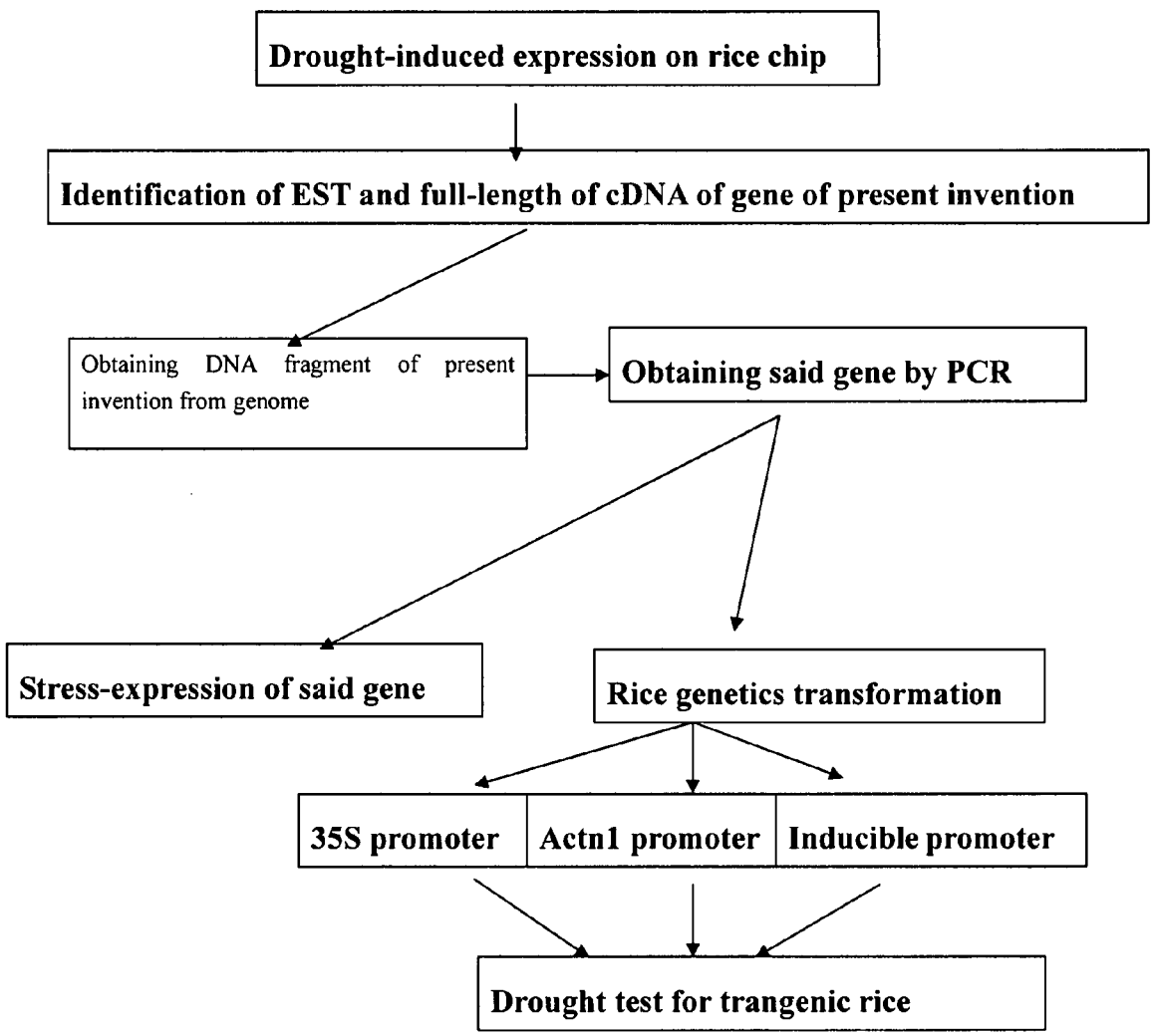
FIG. 1: The flow chart of isolation and identification of OsNACx gene.

The present invention is further demonstrated with examples in combination with figures, and describes methods for isolating and cloning the DNA fragment comprising the whole encoding region of OsNACx gene and for verifying the function of OsNACx gene, based on the initial researches of the present invention (the procedure of invention is shown in FIG. 1).

According to the following description and examples, a skilled in the art can determine the basic technical features of the present invention, and can make any change and modification to the present invention without leaving the spirit and scope of the present invention in order to adapt to various uses and conditions.

Example 1

Separation and Cloning OsNACx Gene and DNA Fragments Containing OsNACx Gene

According to the analysis on expression profile of drought inducible gene of the rice variety "Zhonghan No. 5" (a rice variety which is provided by Shanghai Agriculture Academy of China and publically used in China), a strongly drought-inducible EST (expression sequence tag) (the expression amount increased at least 3.5 times after drought stress) was found, and the analysis of its sequence indicated that this gene was a member of the transcription factor family NAC and was a sequence at the 5' end portion.

The corresponding cDNA clone J012130D02 was found out by searching the Japan rice span database (see on the World Wide Web at cdna01.dna.affrc.go.jp) and located at the 3rd chromosome BAC clone AC135594. According to the BAC clone sequence AC135594, its promotor region is predicted, and its primers PF(5-CAGAATTCAAAGCAA-CAGTGGAGAGAAAAC (SEQ ID NO:8), sequence-specific primer plus joint EcoRI site) and FR(5-TAGGATCCCCGAGCCATCTCTTGAC (SEQ ID NO:9), sequence specific primer plus joint BamHI) were designed. The sequence of 9781-12321bp of BAC clone AC135594 was amplified from the total DNAs of the rice variety "Zhonghan No. 5", and the amplification product was the sequence 1-2540 bp of the present invention (FIG. 3).

The specific steps comprised: extracting the total DNAs from the rice variety "Zhonghan No. 5" (CTAB Extraction Method, Zhang, et al, genetic diversity and differentiation of *indica* an *japonica* rice detected by RFLP analysis, 1992, Theor Appl Genet, 83, 495-499) as the templates for amplification, wherein the reaction conditions were: predegeneration at 94° C. for 3 min; 94° C. for 30 sec, 55° C. for 30 sec, 72° C. for 3 min, 30 circulations; and elongation at 72° C. for 5 min; linking the amplification product of PCR to pGEM-T vector (bought from Promega & co.); and screening and sequencing (ABI3730 sequencer) positive clones to obtain the desired DNA fragment comprising OsNACx gene region and the predicted self-promoter. This clone is designated as PGEM-NAC-PRO.

The total RNAs were extracted from the rice variety "Zhonghan No. 5" with TRIZOL reagent (Invitrogen & co.) after drought-stress treatment (the extraction was conducted according to the TRIZOL reagent specification). By using a reverse transcriptase (Invitrogen & co.), the first-strand of cDNA was synthesized by its reverse transcription, wherein the reaction conditions were: 65° C. for 5 min, 42° C. for 50 min, 70° C. for 10 min. By using the nest primers FF(5-TAGGTACCAGAAGCAAGCAAGAAGCGAT (SEQ ID NO:10), plus joint KpnI) and FR(5-TAGGATCCCCGAGC-CATCTCTTGAC (SEQ ID NO:9), plus joint BamHI), it was amplified from the inverse transcription products, wherein the reaction conditions were: predegeneration at 94° C. for 3 min; 94° C. for 30 sec, 55° C. for 30 sec, 72° C. for 3 min, 30 circulations; elongation at 72° C. for 5 min. The PCR products obtained by the amplification were linked to pGEM-T vector (Promega & co.), and a positive clone was screened and sequenced to obtain the desired full-length gene. The said clone was designated as PGEM-OsNACx.

Example 2

Detection of Inducible Expression of Rice Endogenous Gene OsNACx

The rice variety "Zhonghan No. 5" was used as material and treated separately with drought, coldness, high-salinity stress as well as ABA during the 3 leaf stage. The drought treatment was conducted by immersing the seedling root in 20% polyethylene glycol (PEG6000) for 0 h, 0.5 h, 1 h, 2 h, 4 h, 6 h, and then sampling. The coldness treatment was conducted by placing the seedling in a 4° C. growth chamber for 0 h, 1 h, 8 h, 12 h, and then sampling. The high-salinity treatment was conducted by immersing the seedling root in 200 mM/L NaCl solution for 0 h, 4 h, 8 h, 16 h, and then sampling. The ABA treatment was conducted by immersing the seedling root in 100 µM/L ABA solution for 0 h, 0.5 h, 3 h, 6 h, 12 h, 24 h, and then sampling. The total RNAs of the leaves were extracted (Trizol reagent from Invitrogen & co.), then subject to RNA membrane transfer (according to the experimental methods of "Molecular Cloning", Science Press, Peking, 1999), and Northern hybrided was conducted by using OsNACx as probe. The result showed that the OsNACx gene cloned in the present invention could be induced to express by drought, high-salinity, coldness and ABA (FIG. 4), and was a stress-associated transcription factor.

Example 3

Construction and Transformation of OsNACx Gene Overexpression Vector

According to the results of Example 2, the OsNACx gene of the present invention could be induced to express by drought, high-salinity, coldness and ABA. In order to further illustrate the function of this gene, it was overexpressed in rice and verified by the phenotype of transgenic plants.

Figure 10:
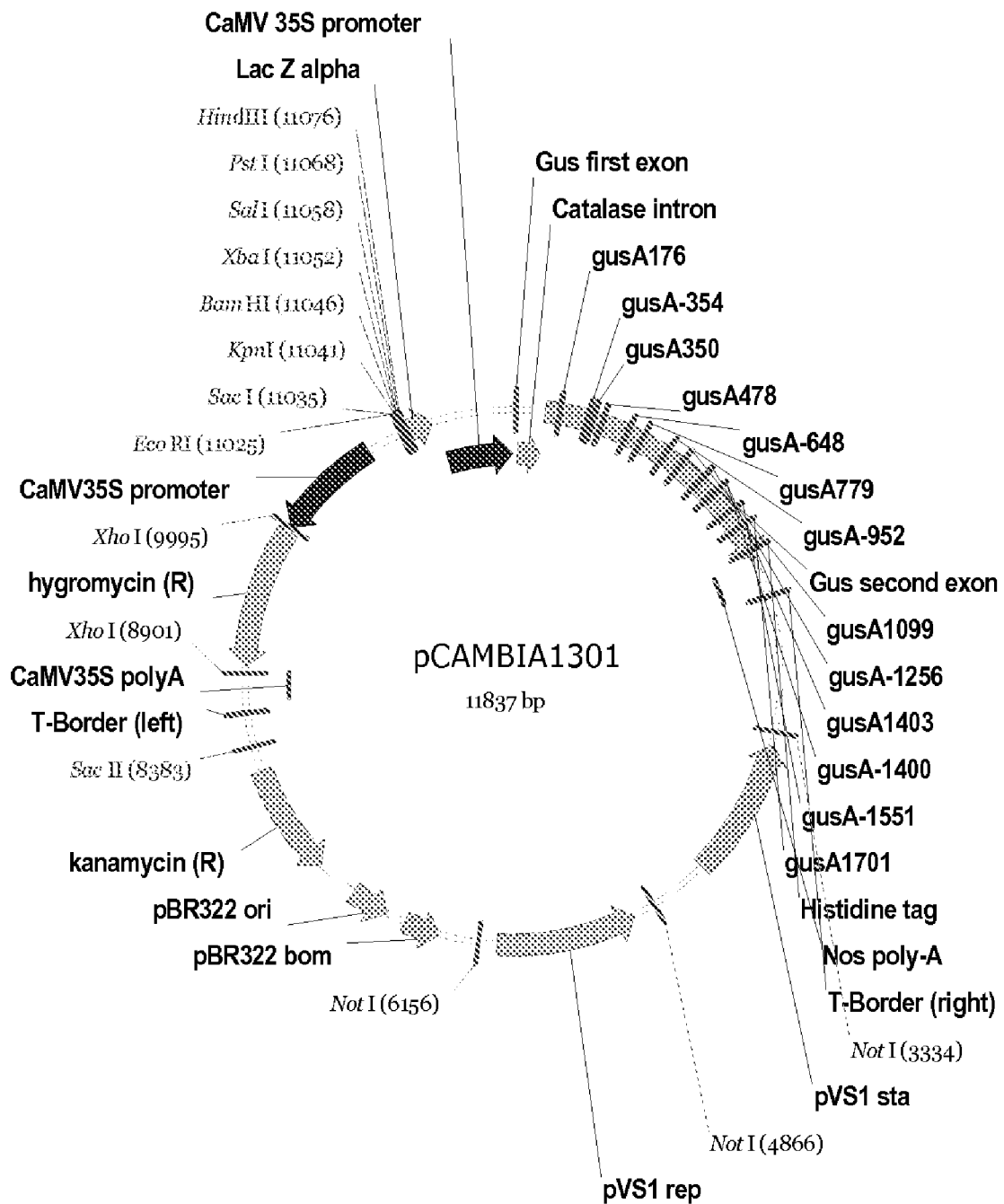
FIG. 10: The structural sketch of overexpression carrier PCAMBIA1301 of the present invention.

The method comprised: enzymatically cleaving the positive clone pGEM-OsNACx plasmid of Example 1 with BamHI and KpnI, and recovering exogenous fragments; in the meantime, enzymatically cleaving the genetic transformation vector pD35S1301 (which is reconstructed based on a common vegetable genetic transformation vector pCAM-BIA1301 from Australia CAMBIA Laboratory (Center for the Application of Molecular Biology to International Agriculture), carries double tobacco mosaic virus promotor 35S with constitutive and over expression characteristics, and is mediated by *Agrobacterium*) by the same way; after cleavage, exacting with chloroform:iso-pentanol (24:1), purifying the enzymatic cleavage product, conducting linkage reaction by using the enzymatic cleavage fragment comprising OsNACx gene and the enzymatically cleaved pD35S1301 vector (see FIG. 10), transforming *E. coli* DH10β(Invitrogen & co.), and screening positive clone by enzymatic cleavage to obtain a transformed vector.

By using the rice genetic transformation system mediated by *Agrobacterium*, it is introduced into the rice variety "Zhong Hua 11" (a rice variety which is provided by China Rice Institute and is publically used in China), and a transgenic plant is then obtained by precultivation, infestation, co-culture, screening the callus with hygromycin resistance, differentiation, rooting, seedling training and transplanting. Based on the method reported by Hiei, et al. (Efficient transformation of rice, *Oryza sativa* L., mediated by *Agrobacterium* and sequence analysis of the boundaries of the T-DNA, 1994, Plant Journal 6:271-282), the rice (*Oryza sativa* L.) mediated by *Agrobacterium* is optimized by a process of mainly using the following steps and reagents.

(1) Abbreviations of Reagents and Solutions

The abbreviations of phytohormones used in culture mediums of the present invention are as follows: 6-BA (6-BenzylaminoPurine); CN (Carbenicillin); KT (Kinetin); NAA (Napthalene acetic acid); IAA (Indole-3-acetic acid); 2,4-D (2,4-Dichlorophenoxyacetic acid); AS (Acetosringone); CH (Casein Enzymatic Hydrolysate); HN (Hygromycin B); DMSO (Dimethyl Sulfoxide); N6max (N6 slather ingredient solution); N6mix (N6 micro constituent solution); Msmax (MS slather ingredient solution); Msmix (MS micro constituent solution)

(2) Formulas of Major Solutions

1) Preparation of N6 Macroelements Mother Liquor (Expressed on the Basis of 10× Concentration):

| | |
|---|---|
| $KNO_3$ | 28.3 g |
| $KH_2PO_4$ | 4.0 g |
| $(NH_4)_2SO_4$ | 4.63 g |
| $MgSO_4 \cdot 7H_2O$ | 1.85 g |
| $CaCl_2 \cdot 2H_2O$ | 1.66 g |

These compounds were dissolved one by one, and diluted to a metered volume of 1000 ml with distilled water at room temperature.

2) Preparation of N6 Microelements Mother Liquor (Expressed on the Basis of 100× Concentration):

| | |
|---|---|
| KI | 0.08 g |
| $H_3BO_3$ | 0.16 g |
| $MnSO_4 \cdot 4H_2O$ | 0.44 g |
| $ZnSO_4 \cdot 7H_2O$ | 0.15 g |

These compounds were dissolved and diluted to a metered volume of 1000 ml with distilled water at room temperature.

3) Preparation of Ferric Salt ($Fe_2EDTA$) Stock Solution (Expressed on the Basis of 100× Concentration):

800 ml double distilled water was prepared and heated to 70° C., then 3.73 g $Na_2EDTA.2H_2O$ was added, fully dissolved, kept in 70° C. water bath for 2 h, diluted to a metered volume of 1000 ml with distilled water, and stored at 4° C. for standby.

4) Preparation of Vitamins Stock Solution (Expressed on the Basis of 100× Concentration):

| | |
|---|---|
| Nicotinic acid | 0.1 g |
| VitaminB1 (Thiamine HCl) | 0.1 g |
| VitaminB6 (Pyridoxine HCl) | 0.1 g |
| Glycine | 0.2 g |
| Inositol | 10 g |

Distilled water was added to a metered volume of 1000 ml, and stored at 4° C. for standby.

5) Preparation of MS Macroelements Mother Liquor (Expressed on the Basis of 10× Concentration):

| | |
|---|---|
| $NH_4NO_3$ | 16.5 g |
| $KNO_3$ | 19.0 g |
| $KH_2PO_4$ | 1.7 g |
| $MgSO_4 \cdot 7H_2O$ | 3.7 g |
| $CaCl_2 \cdot 2H_2O$ | 4.4 g |

These compounds were dissolved at room temperature and diluted with distilled water to a metered volume of 1000 ml.

6) Preparation of MS Microelements Mother Liquor (Expressed on the Basis of 100× Concentration):

| | |
|---|---|
| KI | 0.083 g |
| $H_3BO_3$ | 0.62 g |
| $MnSO_4 \cdot 4H_2O$ | 0.86 g |
| $Na_2MoO_4 \cdot 2H_2O$ | 0.025 g |
| $CuSO_4 \cdot 5H_2O$ | 0.0025 g |

These compounds were dissolved at room temperature and diluted with distilled water to a metered volume of 1000 ml.

7) Preparation of 2,4-D Stock Solution (Expressed on the Basis of 1 mg/ml):

100 mg 2,4-D was weighed and dissolved in 1 ml 1N potassium hydroxide for 5 minutes, then 10 ml distilled water was added for complete dissolution, the solution was diluted with distilled water to a metered volume of 100 ml and stored at room temperature.

8) Preparation of 6-BA Stock Solution (Expressed on the Basis of 1 mg/ml):

100 mg 6-BA was weighed and dissolved in 1 ml 1N potassium hydroxide for 5 minutes ago, then 10 ml distilled water was added for complete dissolution, and the solution was diluted with distilled water to a metered volume of 100 ml and stored at room temperature.

9) Preparation of Naphthylacetic Acid (NAA) Stock Solution (Expressed on the Basis of 1 mg/ml):

100 mg NAA was weighed and dissolved in 1 ml 1N potassium hydroxide for 5 minutes, then 10 ml distilled water was added for complete dissolution, and the solution was diluted with distilled water to a metered volume of 100 ml and stored at 4° C. for standby.

10) Preparation of Indoleacetic Acid (IAA) Stock Solution (Expressed on the Basis of 1 mg/ml):

100 mg IAA was weighed and dissolved in 1 ml 1N potassium hydroxide for 5 minutes, then 10 ml distilled water was added for complete dissolution, and the solution was diluted with distilled water to a metered volume of 100 ml and stored at 4° C. in a triangular flask with 300 ml distilled water and 2.78 g FeSO$_4$.7H$_2$O. 300 ml distilled water was added in another triangular flask for standby.

11) Preparation of Glucose Stock Solution (Expressed on the Basis of 0.5 g/ml):

100 mg of glucose was weighed and dissolved and diluted with distilled water to a metered volume of 250 ml, and stored at 4° C. after sterilization.

12) Preparation of AS Stock Solution:

0.392 g of AS and 10 ml DMSO were packaged in a 1.5 ml centrifugal pipe, and then stored at 4° C. for standby.

13) Preparation of 1N Stock Solution:

5.6 g potassium hydroxid was weighed, dissolved and diluted with distilled water to a metered volume of 100 ml, and stored at room temperature for standby.

(3) Culture Medium Formula for Genetic Transformation of Rice

1) Induction Culture Medium:

| N6max mother liquor (10X) | 100 ml |
| N6mix mother liquor (100X) | 10 ml |
| Fe$^{2+}$EDTA stock solution (100X) | 10 ml |
| Vitamins stock solution (100X) | 10 ml |
| 2,4-D stock solution | 2.5 ml |
| Proline | 0.3 g |
| CH | 0.6 g |
| Sucrose | 30 g |
| Phytagel | 3 g |

Distilled water was added to 900 ml, and pH value was adjusted to 5.9 with 1N potassium hydroxide, then the medium was boiled and diluted to a metered volume of 1000 ml, and subpackaged in 50 ml triangular flasks (25 ml/flask), sealed and sterilized.

2) Secondary Culture Medium:

| N6max mother liquor (10X) | 100 ml |
| N6mix mother liquor (100X) | 10 ml |
| Fe$^{2+}$EDTA stock solution (100X) | 10 ml |
| Vitamins stock solution (100X) | 10 ml |
| 2,4-D stock solution | 2.0 ml |
| Proline | 0.5 g |
| CH | 0.6 g |
| Sucrose | 30 g |
| Phytagel | 3 g |

Distilled water was added to 900 ml, the pH value was adjusted to 5.9 with 1N potassium hydroxide, then the medium was boiled and diluted to a metered volume of 1000 ml, subpackaged in 50 ml triangular flasks (25 ml/flask), sealed and sterilized.

3) Pre-Cultured Medium:

| N6max mother liquor (10X) | 12.5 ml |
| N6mix mother liquor (100X) | 1.25 ml |
| Fe2+EDTA stock solution (100X) | 2.5 ml |
| Vitamins stock solution (100X) | 2.5 ml |
| 2,4-D stock solution | 0.75 ml |
| CH | 0.15 g |
| Sucrose | 5 g |
| Agarose | 1.75 g |

Distilled water was added to 250 ml, and pH value was adjusted to 5.6 with 1N potassium hydroxide, then the medium was sealed and sterilized. Before using, the medium was heated and melted, 5 ml glucose stock solution and 250 μl AS stock solution were added, then the medium was pured into culture dishes (25 ml/dish). pH=5.6.

4) Cocultivation Medium:

| N6max mother liquor (10X) | 12.5 ml |
| N6mix mother liquor (100X) | 1.25 ml |
| Fe$^{2+}$EDTA stock solution (100X) | 2.5 ml |
| Vitamins stock solution (100X) | 2.5 ml |
| 2,4-D stock solution | 0.75 ml |
| CH | 0.2 g |
| Sucrose | 5 g |
| Agarose | 1.75 g |

Distilled water was added to 250 ml, pH value was adjusted to 5.6 with 1N potassium hydroxide, and the medium was sealed and sterilized. Before using, was heated and melted, 5 ml glucose stock solution and 250 μl AS stock solution were added, then the medium was pured into culture dishes (25 ml/dish).

5) Suspension Medium:

| N6max mother liquor (10X) | 5 ml |
| N6mix mother liquor (100X) | 0.5 ml |
| Fe$^{2+}$EDTA stock solution (100X) | 0.5 ml |
| Vitamins stock solution (100X) | 1 ml |
| 2,4-D stock solution | 0.2 ml |
| CH | 0.08 g |
| Sucrose | 2 g |

Distilled water was added to 100 ml, pH value was adjusted to 5.4, and then the medium was subpackaged in two triangular flasks, sealed and sterilized. Before using, 1 ml glucose stock solution and 100 μl AS stock solution were added.

6) General Medium for Select Culture Medium:

| N6max mother liquor (10X) | 25 ml |
| N6mix mother liquor (100X) | 2.5 ml |
| Fe$^{2+}$EDTA stock solution (100X) | 2.5 ml |
| Vitamins stock solution (100X) | 2.5 ml |
| 2,4-D stock solution | 0.625 ml |
| CH | 0.15 g |
| Sucrose | 7.5 g |
| Agarose | 1.75 g |

Distilled water was added to 250 ml, pH value was adjusted to 6.0, and then the medium was sealed and sterilized. Before using, the medium was dissolved, 250 μl hygromycin (50 mg/ml) and 400 ppm carbenicillin (CN) were added, and then the medium was subpackaged in culture dishes (25 ml/dish).

7) Pre-Differentiation Medium:

| N6max mother liquor (10X) | 25 ml |
| N6mix mother liquor (100X) | 2.5 ml |
| Fe2+EDTA stock solution (100X) | 2.5 ml |
| Vitamins stock solution (100X) | 2.5 ml |
| 6-BA stock solution | 0.5 ml |
| KT stock solution | 0.5 ml |

-continued

| | |
|---|---|
| NAA stock solution | 50 μl |
| IAA stock solution | 50 μl |
| CH | 0.15 g |
| Sucrose | 7.5 g |
| Agarose | 1.75 g |

Distilled water was added to 250 ml, pH value was adjusted to 5.9 with 1N potassium hydroxide, and then the medium was sealed and sterilized. Before using, 250 μl hygromycin (50 mg/ml) and 200 ppm carbenicillin (CN) were added, and then the medium was subpackaged in culture dishes (25 ml/dish).

8) Differentiation Medium:

| | |
|---|---|
| N6max mother liquor (10X) | 100 ml |
| N6mix mother liquor (100X) | 10 ml |
| $Fe^{2+}$EDTA stock solution (100X) | 10 ml |
| Vitamins stock solution (100X) | 10 ml |
| 6-BA stock solution | 2 ml |
| KT stock solution | 2 ml |
| NAA stock solution | 0.2 μl |
| IAA stock solution | 0.2 μl |
| CH | 1 g |
| Sucrose | 30 g |
| Phytagel | 3 g |

Distilled water was added to 900 ml, pH value was adjusted to 6.0 with 1N potassium hydroxide. The medium was then boiled and diluted to a metered volume of 1000 ml, and subpackaged in 50 ml triangular flasks (25 ml/flask), sealed and sterilized.

9) Rooting Culture Medium:

| | |
|---|---|
| MSmax mother liquor (10X) | 50 ml |
| MSmix mother liquor (100X) | 5 ml |
| Fe2+EDTA stock solution (100X) | 5 ml |
| Vitamins stock solution (100X) | 5 ml |
| Sucrose | 30 g |
| Phytagel | 3 g |

Distilled water was added to 900 ml, and pH value was adjusted to 5.8 with 1N potassium hydroxide. The medium was then boiled and diluted to a metered volume of 1000 ml, and subpackaged in rooting tubes (25 ml/tube), sealed and sterilized.

(4) Steps of Genetic Transformation Mediated by *Agrobacterium* (Specific Examples of Using the Above-Mentioned Culture Mediums)

3.1 Callus Induction (1) Mature rice seeds of "ZHONGHUA 11" were deshelled, then treated with 70% alcohol for 1 minute and disinfected the surface of the seeds with 0.15% $HgCl_2$ for 15 minutes in order;
(2) The seeds were washed with sterilized water for 4-5 times;
(3) The seeds were put on the above-mentioned induction medium;
(4) The inoculated medium was placed in darkness and cultured for 4 weeks at 25±1° C. to obtained rice callus 3.2 Callus Subculture The bright yellow, compact and relatively dry embryogenic callus was selected, put onto the above-mentioned subculture medium, and cultured in darkness for 2 weeks at 25±1° C. to obtained rice callus.

3.3 Pre-Culture

The compact and relatively dry rice embryogenic callus was selected, put onto the above-mentioned pre-cultured medium, and cultured in darkness for 2 weeks at 25±1° C.

3.4 *Agrobacterium* Culture (1) *Agrobacterium* EHA105 (Invitrogen & co.) was pre-cultured on LA culture medium (a publicly used medium) with corresponding resistance at 28° C. for 48 h (2 days);
(2) The *Agrobacterium* was transferred to the above-mentioned suspension medium and cultured in a shaking table at 28° C. for 2-3 hours.

3.5 *Agrobacterium* Infection (1) The pre-cultured callus was transferred into a sterilized bottle;
(2) The above said *Agrobacterium* was regulated to $OD_{600}$ 0.8-1.0;
(3) The rice callus was immersed in the *Agrobacterium* suspension for 30 minute;
(4) The callus of step (3) was transferred on sterilized filter paper and dried, and then cultured onto the above-mentioned cocultivation medium for 72 h (3 days) at 19-20° C.

3.6 Washing and Select Culture of Callus (1) The rice callus was washed with sterilized water until no agrobacrium was observed;
(2) The rice callus of step (1) was immersed in sterilization water containing 400 ppm carbenicillin (CN) for 30 minutes;
(3) The callus of step (2) was transferred on sterilized filter paper and dried;
(4) The callus of step (3) was transferred on the above-mentioned select medium and select-cultured for 2-3 times, 2 weeks for each time (The above-mentioned select medium was heated and melted, then cooled to about 60° C., and appropriate hygromycin and carbenicillin were added. The screening concentration was 400 mg/l for hygromycin and 400 mg/l for carbenicillin in the select medium for the first culture, and was 250 mg/l for hygromycin and 250 mg/l for carbenicillin in the select medium for the second and following cultures.)

3.7 Differentiation (1) The resistant rice callus obtained from the aforementioned select culture medium was transferred to the pre-differentiation medium, and cultured in darkness for 5-7 weeks;
(2) The rice callus obtained from the pre-differentiation culture of step 1 was transferred to the differentiation medium, and cultured in lighting at 19-20° C. to obtain a transgenic rice plant.

3.8 Rooting (1) The roots of transgenic rice plant generated during the differentiation were cut off;
(2) The plant was then transferred to rooting culture medium, and cultured in lighting at 26° C. for 2-3 weeks.

3.9 Transplantation

The residual medium on roots of the transgenic rice plant was washed off, the seedling with good roots was transferred in greenhouse, and moisture was maintained in primal days.

The obtained transgenic rice plant was designated as T40SN (wherein T40S represents the vector number, N represents the transgenic rice variety "ZHONGHUA 11"). Finally, 36 independent transgenic rice plants were obtained.

Example 4

Drought Screening of the OsNACx Gene Transgenic T1 Family in Field

Figure 5:
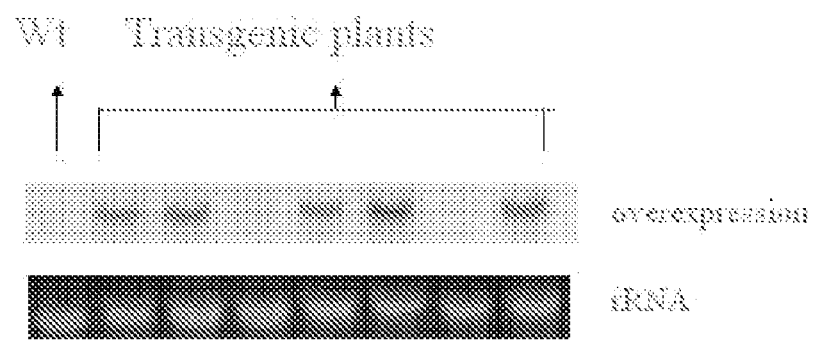
FIG. 5: The expression situations of OsNACx gene in transgenic plants (the first is control, and the residues are transgenic and independent transgenic plants).

In order to verify whether the drought resistance of transgenic rice is related to OsNACx gene, the expression of OsNACx gene in some transgenic rice plants in the present invention was detected by Northern hybridization technology (FIG. 5 showed the Northern hybridization results, wherein the method was the same as Example 2). In the meantime, the screening of T1 generation plants with drought resistance of the present invention was conducted in field by the following steps. The seeds of every family of T1 generation were immersed into an aqueous solution of hygromycin (50 mg/ml), non-sprouting seeds were removed, other seeds were seeded in seedling bed, and rice seedlings in 5 leaf stage were transplanted to a sandy land in an anti-drought greenhouse, where 20 individual plants of each transgenic family were planted in 2 rows, and water supply was stopped in 3 weeks before heading stage. FIG. 6 showed the drought screening results of transgenic families and the control under drought stress for 22 days. The experiment results showed that the drought resistance of transgenic plants was significantly higher than that of the control. The detection of relative water content of two families were 83.9% and 85.2%, respectively, which indicated that the relative water content was not apparently different, so that the OsNACx gene was assuredly relative to drought resistance, and the overexpression of the gene could improve the drought resistance of transgenic plants. In order to further demonstrate that the gene of the present invention can improve the drought resistance of transgenic plants, the fruit ratio of transgenic families under drought stress was analyzed. The statistical data showed that the fruit ratio of overexpression transgenic plants was apparently higher than that of the control, and the fruit ratio increased from 1.8% to 25% (as shown in Table 1), while the number of tillers and the weight of thousand grains had not apparently difference, which proved in another aspect that OsNACx gene was assuredly related to the enhancement of drought resistance.

TABLE 1

Comparison of fruit ratio between transgenic families and the control under drought stress

| Rice Family | Number of Plants | Average Fruit Ratio of single plant (%) | Standard Deviation | Significant Difference Compare to Control |
|---|---|---|---|---|
| CK | 5 | 1.78 | 0.71 | — |
| T40S8 | 5 | 24.04 | 3.39 | Significant($p < 0.001$) |
| T40S24 | 5 | 23.97 | 3.46 | Significant($p < 0.001$) |
| T40S25 | 5 | 22.97 | 3.14 | Significant($p < 0.001$) |
| T40S19 | 5 | 31.87 | 6.06 | Significant($p < 0.001$) |
| T40S21 | 5 | 23.34 | 2.77 | Significant($p < 0.001$) |

Example 5

High-Salinity Resistance Screening of OsNACx Gene Transgenic T1 Family in Seedling Stage According to Example 4, it was proved that the drought resistance of OsNACx transgenic plants in adult stage was apparently higher than that of the control. In order to verify other stress-resistances of OsNACx transgenic rice, it was treated with high-salinity stress in seedling stage.

The specific method was as follows: transgenic overexpression plants of five families in T1 generation were selected, the T1 generation seeds were immersed into an aqueous solution of hygromycin (50 mg/ml), non-sprouting seeds were removed, and other seeds were seeded in small round buckets (the soil used in the experiments was a mixture of south rice soil and sands in a ratio of 2:3; isometric water to equivalent soil was added in each bucket; and the water naturally leaked out to ensure the consistency of soil compactness). The experiment was repeated for 3 times. The healthy plants in 5 leaf stage was treated with high-salinity stress (200 mM NaCl solution) until all control plants died, and the survival rate of the plants were observed (individual plant with less than 20% green leaf area was usually difficult to survive and deemed to be dead). FIG. 7 showed the growth condition of overexpression transgenic family when the control plants all died under the stress for 12 days. The table 2 showed the survival rate of every overexpression transgenic family when the control plants all died. The survival rate of every transgenic family was usually higher than 80%. The result showed that OsNACx transgenic plants could improve the resistance of plants to high-salinity.

TABLE 2

Survival rate (%) of every transgenic family under high-salinity stress for 12 days

| Rice Family | Repeated Number | Survival Number/Total Number | | | Survival Rate |
|---|---|---|---|---|---|
| TA0S25 | 3 | 21/24 | 23/27 | 24/29 | 85.1 ± 2.4 |
| T40S24 | 3 | 20/26 | 24/28 | 23/27 | 82.6 ± 4.9 |
| T40S21 | 3 | 18/21 | 21/24 | 19/26 | 82.1 ± 7.9 |
| T40S8 | 3 | 25/27 | 24/28 | 26/30 | 88.3 ± 3.7 |
| T40S19 | 3 | 21/23 | 25/27 | 24/29 | 88.9 ± 5.3 |

Example 6

Verification of the Transcription Activity of OsNACx Gene 3' End

Since the gene of the present invention was an inducible transcription factor, it should possess function of transcriptional activation, and could activate the downstream gene expression under stress in order to generate resistance. In order to verify whether the OsNACx gene of the present invention has the function of transcriptional activation, or which region possesses the function, a yeast system was used in a trans-activation experiment in the present example.

Figure 8:
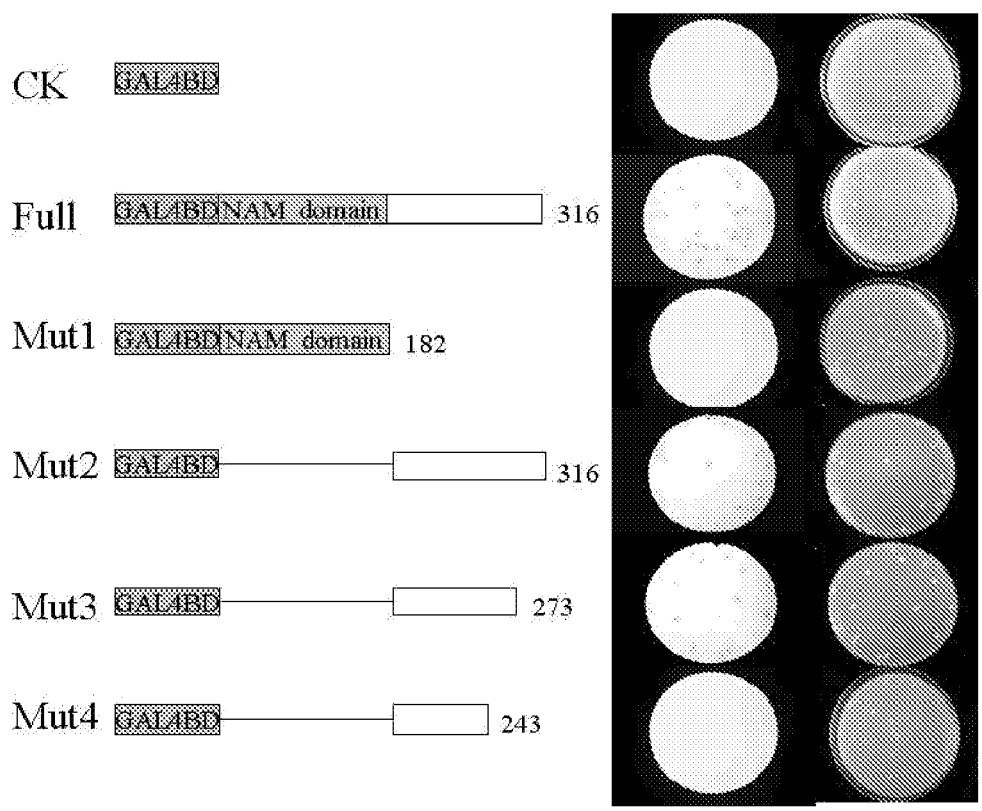
FIG. 8: Trans-activation activity of OsNACx gene which is tested according to the expression of LacZ reporter gene after a yeast cell is transformed by OsNACx gene.

Firstly, a series of OsNACx gene and partial deletion muton to yeast GAL4-DB fusion expression vector pDEST32 (Invitrogen & co.) were constructed, and used to transform yeast cell Y187 (CLONTHCH & co.). In the β-Galactosidase activity test, the expression of reporter gene LacZ was determined based on whether the yeast showed blue color. The results showed that the OsNACx gene really possessed function of transcriptional activation, and the activation functional domain was located at the 3' end of the gene, and the amino acid sequence from 243 to 273 was necessary for the function of transcriptional activation of the present gene. FIG. 8 showed the expression situation of reporter gene LacZ in yeast cell transformed by OsNACx gene or by partial deletion muton thereof, wherein CK represents yeast cell Y187 transformed by empty vector pDEST32; Full represents yeast cell Y187 transformed by pDEST32 fused with full length OsNACx gene; Mut1 represents yeast cell Y187 transformed by pDEST32 fused with 1-166AA fragment (NAM domain) of OsNACx gene; Mut2 represents yeast cell Y187 transformed by pDEST32 fused with 182-316AA fragment of OsNACx gene; Mut3 represents yeast cell Y187 transformed by pDEST32 fused with 182-273AA fragment of OsNACx gene; Mut4 represents yeast cell Y187 transformed by pDEST32 fused with 182-243AA fragment of OsNACx gene.

The specific method was as follows:

1. The Full Length OsNACx Gene and Partial Deletion Muton Thereof were Fused to the Yeast Expression Vector pDEST32 (Invitrogen & Co.).

According to the reading frame of pDEST32 carrier and the full length cDNA xx sequence, the following gene primers were designed (by using software primer 5.0), respectively:

```
DBF:   5-AGAAGCAAGCAAGAAGCGAT        (SEQ ID NO: 11)

DBR:   5-CCGAGCCATCTCTTGAC           (SEQ ID NO: 12)

DBM1R: 5-TCCGACACAGCACCCAATCATC      (SEQ ID NO: 13)

DBM3R: 5-TATCGTCGTAGCTCAGGTCCA       (SEQ ID NO: 14)

DBM4R: 5-CTTTCTTGGGCACCATCAT         (SEQ ID NO: 15)

DBM5R: 5-ACGGGAAGGGGTCGTTGTCCA       (SEQ ID NO: 16)

DBMF:  5-CTGTACAACAAGAAGAACG         (SEQ ID NO: 17)
```

The joint attB1 (5-ggggacaagtttgtacaaaaaagcaggct, SEQ ID NO:18) was then added to the front-ends of primers DBF and DBMF; and the joint attB2 (5-ggggaccactttgtacaagaaagctgggt, SEQ ID NO:19) was added to the front-ends of primers DBR, DBM1R, DBM3R, DBM4R and DBM5R. Under the reaction conditions: predegeneration at 94° C. for 3 min; 94° C. for 30 sec, 55° C. for 30 sec, 72° C. for 3 min, 30 circulations; elongation at 72° C. for 5 min, the product of the combination of primers DBF and DBMF was DBNACF (1-316AA), the product of primers DBF and DBM1R was Mut1 (1-182AA), the product of primers DBMF and DBR was Mut2 (182-316AA), the product of primers DBMF and DBM3R was Mut3 (182-273AA), and the product of primers DBMF and DBM4R was Mut4 (182-243AA). The obtained PCR products were purified through PEG8000, and then subject to BP recombination reaction with intermediate vector pDONR221 (Invitrogen & co.), wherein the reaction system were 5 ul, 200 ng PCR product, 50 ng pDONR221, 2 ul 5XBP Clonase Reaction Buffer, and 2 ul BP Clonase Mix. The *E. coli* DH10β (Invitrogen & co.) was transformed at 25° C. for 5 h, positive clones were screened, and then the gene fragment carried by the desired positive clone plasmid was fused to yeast expression vector pDEST32 by LR recombination reaction, wherein the steps comprised: *E. coli* DH10β (Invitrogen & co.) was transformed under conditions of 100 ng positive plasmid of BP reaction, 50 ng pDEST32, 2 ul 5XLR Clonase Buffer, 2 ul LR Clonase Mix, at 25° C. for about 5 h, and positive clones were screened.

2. Preparation and Transformation of Yeast Competent (Clontech, Yeast Protocols Handbook) by Lithium Acetate (LiAc) Method 1) Reagent and Formula A. YPD nutrient solution:

| | |
|---|---|
| 20 g | Difco peptone |
| 10 g | extractive of yeast |
| 20 g | glucose | diluted to a metered volume of 1000 ml with distilled water, and sterilized for 15 minute.

B. SD/Leu culture solution:

| | |
|---|---|
| 6.7 g | yeast nitrogenous base without amino acid |
| 20 g | agar powder |
| 20 g | glucose |
| 0.69 g | Leu DO Supplement (CLONTECH & co.) | diluted to a metered volume of 1000 ml with distilled water, and sterilized for 15 minute.

C. 10TE buffer solution:
0.1M Tris-HCl, 10 mM EDTA, pH 7.5, sterilized

D. 10LiAc:
1M lithium acetate, pH 7.5, sterilized

E. PEG/LiAc Solution:

| | Final concentration | For preparation 10 ml solution |
|---|---|---|
| PEG4000 | 40% | 8 ml 50% PEG |
| TE buffer solution | 1x | 1 ml 10x TE |
| LiAc | 1x | 1 ml 10x LiAc |

2) Procedure:

A. Yeast single colonies with diameter of 2-3 mm were scattered by 1 ml YPD solution, and then transferred to a triangular flask containing 10 ml YPD medium.

B. Cultured under the rotation of 250 rpm at 30° C. for 16-18 h, so that OD600>1.5.

C. 5 ml the above-mentioned yeast solution was transferred to another triangular flask containing 50 ml YPD medium and detected concentration to get OD600=0.2-0.3.

D. Cultured at 30° C. for 3 h (230 rpm), OD600=0.4-0.6 (if OD600<0.4, the culture maybe get in trouble).

E. The yeast solution was transferred into a 50 ml centrifuge tube, and centrifuged at 1000×g for 5 minute at room temperature.

F. The supernatant was removed, the cells was suspended with sterilized double distilled water again, and centrifuged at 1000×g for 5 minute at room temperature.

G. The supernatant was removed, the yeast cells were mixed homogenously with 1×TE/1×LiAc that was prepared in situ.

H. 200 ng fusion plasmid DNA was transferred into a 1.5 ml centrifuge tube, and 100 ul yeast competent cells were added and mixed homogeneously, then 600 ul PEG/LiAc was added, centrifuged at high speed, and cultured at 30° C. for 30 min (200 rpm).

I. 70 ul DMSO (100%) was added, cantabily reversed for several times, placed in 42° C. water bath for 15 min, and then placed on ice for 2 min.

J. Centrifuged at 14000 rpm for 5 sec at room temperature, the supernatant was removed, and the yeast cells were scattered with 1×TE buffer.

K. 100 ul transformed cells were coated on Leu/SD plate, inversion cultured in 30° C. incubator for 2-4 days, until clones appeared.

3. Verification of Transcription Activity of OsNACx Gene and Partial Deletion Muton Thereof Based on the Expression of Reporter Gene LacZ in Beta-Galactosidase Experiment 1) Reagent and Formula
A. Z buffer solution

| | |
|---|---|
| $Na_2HPO_4 \cdot 7H_2O$ | 16.1 g/L |
| $NaH_2PO_4 \cdot H_2O$ | 5.5 g/L |
| KCl | 0.75 g/L |
| $MgSO_4 \cdot 7H_2O$ | 0.246 g/L |

Regulated pH to 7.0, and sterilized.
B. X-gal stock solution (20 mg/ml)
C. Z buffer solution/X-gal solution:
100 ml Z buffer solution:
0.27 ml β-mercaptoethanol
1.67 ml X-gal stock solution 2) Procedure:
A. The transformed clone grew to 1-3 mm (30° C., 2-4 days).

B. Round Watman filter paper with appropriate size was placed on 10 cm asepsis plate, and about 2.5-5 ml Z buffer/X-gal solution was added to wet the filter paper, and bubble was avoided.

C. Another clean asepsis filter paper was moved by forceps to place on the plate with growing clone, and the filter paper was slightly pressed in order to adhere the clone to the filter paper.

D. When the filter paper was wetted, it was opened with forceps, and the surface with clone was upward, then the filter paper was placed into liquid nitrogen for 10 sec, and thawed at room temperature in order to crash the yeast cells.

F. The filter paper which surface with clone was upward was carefully placed onto the previously wetted filter paper, and bubble was avoided.

G. The filter paper was placed at 30° C. (30 min-8 hr), and the activation function of the gene was judged according to the occurrence of blue spot.

Example 7

Functional Verification of OsNACx Genic Promotor and it's Subcellular Localization In order to confirm the expression location of OsNACx gene in cell and the activity of it's self promotor (1-1374 bp), the construction of GFP-NLS (nuclear location signal) fusion protein was further performed, and the gene expression profile was determined according to the expression of GFP. First, the published documents about *Arabidopsis thaliana* NAC gene (Miki Fujita, Kazuo Shinozaki et al., A Dehydration-induced NAC protein, RD26, is involved in a novel ABA-dependent stress-signaling pathway. Plant J (2004), 39, 863-876) were used. It was deduced that the nuclear location signal (NLS) of the gene may locate at 79-90AA or 116-182AA, and the subcellular location of the gene could be determined according to the expressive region of this sequence fused with GFP in cell.

Figure 11:
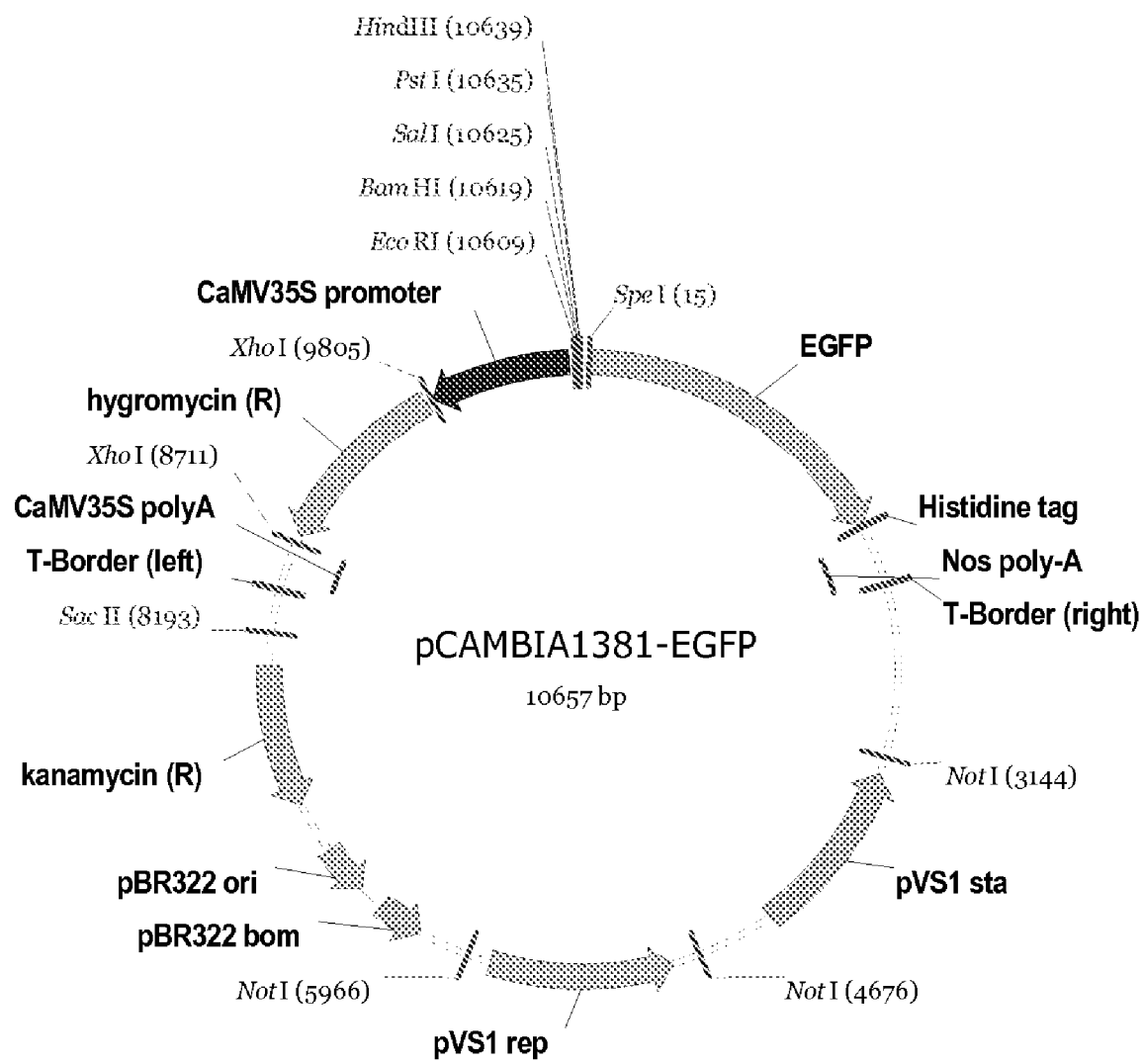
FIG. 11: The structural sketch of subcellular localization carrier PCAMBIA1381-EGFP of the present invention.

The 1-1641 bp fragment (including first 1374 bp of ATG and gene 1-90AA, i.e, including promotor region and nuclear location signal) was fused with pCAMBIA1381-GFP vector. It was expected that 1-1374 bp of the fragment had already contained an intact promotor which could promote the expression of gene, and that the 1-99AA sequence (including the nuclear location signal) of the gene was included so that the expressive condition of the gene in cells could be determined according to the expressive location of GFP. The pCAMBIA1381-EGFP vector was reconstructed (see FIG. 11) based on pCAMBIA1381 (a plant genetic transcription vector commonly used in the world), wherein the carried GUS gene was replaced with GFP gene, and no promoter was before the GFP gene. The pCAMBIA1381 vector was from Australia CAMBIA Laboratory (Center for the Application of Molecular Biology to International Agriculture).

The specific method for the construction of vector for the fused gene was as follows. The primers PF (5-cagaattcaaagcaacagtggagagaaaac (SEQ ID NO:8), added with joint EcoRI site) and PR (5-caaagcttgcgtgacccattaggatactt (SEQ ID NO:20), added with joint HindIII) were designed, then the total DNAs of rice variety "Zhonghan No. 5" or the vector pGEM-NAC-PRO constructed in Example 1 were used as template, and the amplification program (predegeneration at 94° C. for 3 min; 94° C. for 30 sec, 55° C. for 30 sec, 72° C. for 3 min, 30 circulations; elongation at 72° C. for 5 min) were employed. The amplification product was enzymatically cleaved by EcoRI and HindIII and linked to the vector pCAMBIA1381-EGFP that was enzymatically cleaved by EcoRI and HindIII as well. The rice callus was transformed with the fusion vector p1381-GFP-promoter-NLS using *Agrobacterium*-mediated gene transformation system (see detailedly in Example 3), the callus with hygromycin resistance was obtained (see Example 3), and the expression of GFP was observed under fluorescence microscope (see FIG. 9A). The result showed that 1-1374 bp of the sequence had already contained the intact promoter, and it could promote expression of the gene.

Figure 9:
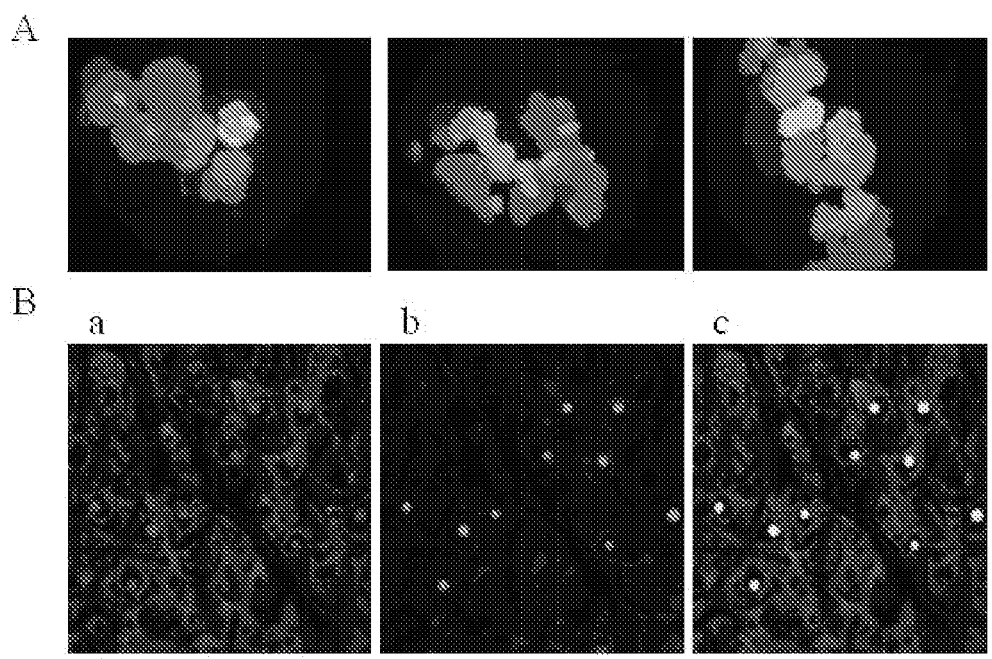
FIG. 9: The subcellular localization and the self-promotor expression of OsNACx gene in plant cells.

In order to localize the gene in cell, the resistance callus was sliced and observed under confocal microscope to determine the intracellular expression condition of GFP. FIG. 9B showed that GFP was expressed only in nuclei under the observation of confocal microscope, which indicated that the sequence 1-99AA had already included NLS so that GFP could be localized in nuclei, i.e., the OsNACx protein was localized in nuclei. This example proved that the sequence 1-1374 bp in the present invention included intact promotor, and it could induce the expression of the gene. In addition, it was speculated that the 79-90AA of OsNACx was NLS, and thus the OsNACx protein was localized in cell nucleus.

What is claimed is:

1. An expression vector comprising a promoter operably linked to a polynucleotide consisting of the nucleotide sequence as shown in positions 1374-2453 of SEQ ID NO:1 or a variant thereof having at least 95% homology to positions 1374-2453 of SEQ ID NO:1, wherein positions 1374-2453 of SEQ ID NO:1 encode a transcription factor providing tolerance to drought and/or salt stress in a plant.

2. A host cell transformed or transfected by the expression vector according to claim 1.

3. The host cell according to claim 2, wherein the cell is from a plant selected from the group consisting of rice, tomato, potato, tobacco, pepper, corn, barley, wheat, *Brassica, Arabidopsis*, sunflower, soybean, poplar and pine.

4. A method for increasing tolerance to drought and/or salt stress in a plant, the method comprising the step of introducing into a plant a polynucleotide comprising the nucleotide sequence as shown in SEQ ID NO:1 or a variant thereof having at least 95% homology to SEQ ID NO:1, wherein SEQ ID NO:1 encodes a transcription factor providing tolerance to drought and/or salt stress in a plant.

5. The method according to claim 4, wherein the plant is selected from the group consisting of rice, tomato, potato, tobacco, pepper, corn, barley, wheat, *Brassica, Arabidopsis*, sunflower, soybean, poplar and pine.

6. The method according to claim 4, wherein the plant is rice.

7. A method for increasing tolerance to drought and/or salt stress in a plant, the method comprising the step of introducing into a plant a polynucleotide comprising the nucleotide sequence as shown in positions 1374-2453 of SEQ ID NO:1 or a variant thereof having at least 95% homology to positions 1374-2453 of SEQ ID NO:1, wherein positions 1374-2453 of SEQ ID NO:1 encode a transcription factor providing tolerance to drought and/or salt stress in a plant.

8. The method according to claim 7, wherein the plant is rice.

\* \* \* \* \*

UNITED STATES PATENT AND TRADEMARK OFFICE
CERTIFICATE OF CORRECTION

PATENT NO. : 7,834,244 B2  
APPLICATION NO. : 11/722298  
DATED : November 16, 2010  
INVENTOR(S) : Hu et al.

Page 1 of 1

It is certified that error appears in the above-identified patent and that said Letters Patent is hereby corrected as shown below:

On Title Page:
Please add the following information:
-- (30)  Foreign Application Priority Data
         Dec. 21, 2004   (CN)   200410061408.6 --

Signed and Sealed this
Twenty-sixth Day of July, 2011

David J. Kappos
*Director of the United States Patent and Trademark Office*

SEQUENCE LISTING

<160> NUMBER OF SEQ ID NOS: 20

<210> SEQ ID NO 1
<211> LENGTH: 2540
<212> TYPE: DNA
<213> ORGANISM: Oryza sativa
<220> FEATURE:
<221> NAME/KEY: gene
<222> LOCATION: (1)..(2540)
<220> FEATURE:
<221> NAME/KEY: exon
<222> LOCATION: (1374)..(1847)
<220> FEATURE:
<221> NAME/KEY: intron
<222> LOCATION: (1848)..(1976)
<220> FEATURE:
<221> NAME/KEY: exon
<222> LOCATION: (1977)..(2453)

<400> SEQUENCE: 1

```
ccaaagcaac agtggagaga aaactaaaaa aaagagaatg cgttagaata tgtcgtggaa      60
taatgggagg ggataagcga tgctgaggta gcggccgaat cttcccgacg cacgccgaac     120
atgcatgata cgagtatatg atttgatttg atgattttttc tggtgccggt accttgaggt     180
tttttttctg tcctgactcc tgagatgaag gaaaaggctc gatcgatgat gcgatcggcg     240
atgatgagag tggtggttcc aagtaacgtg ggggaaatct cgtctctcgg cgcaatgcta     300
taaacatgcg gatgaccatc accggagtaa gtagagtaat ttagtcgtac ttgtacctac     360
tggaacagtg accacccaac gagcctcaca ttcactgaat catactagtc gtactactac     420
tactacaaca ctggaacgga tagaaaacga taaatgacgc cgcataatcg acaacgcatg     480
ggaccaaact catgcttatc tgctcttgta ctcgtgctta tctcaaatcc acctcatttt     540
acatgcccct ttttgccaca gcaactttcg gtcccatcat ggcatatttg caaacgcaaa     600
atagtttata aataaaattt tttatatgcg tgttttttata gtgatataaa agcaacggtt     660
gaaagataaa tttcgataaa aaaaccttaa aatcagcttt aaatttaaga ttaaaaattt     720
aaattttgac tgataataag tattagcgaa aagatgatgt cctaatttcc ccttttcgct     780
ccaccccatg acgttgtccg acatctaaat actactccta atcaacttgc aacctaagat     840
aatttagtat agtacacgta gtacagcctt tttggagcag taacaaaaga cgcgcgggcc     900
acacgtccgt gcagttgcag ccgccgctgc atccccaccg cgaaaaccac ggcaaaattt     960
agcggcggcc gctgtggccg cctcaccccc ccgcgcctgg ctgtccacag caacgcacgc    1020
acccgcaccc gcaccgccga cccgaccgcg gcgccgagct gtcccaattc tgctgacctc    1080
ggccgtgacg ccatcctcgc acgggtccaa tccccgacgc aggaggtggc ctccttcctc    1140
gaaacccacc acctcaccac cacacgtgcc ccatttcatc ccatctcctc ttcttcccgc    1200
agccgccgac tccgctttga ctcatccccc cgccgccgaa ccttcagac tacctccctc    1260 tatatatccc cccctccgcc cgccatttct ccccattcga gaaatccctc acaacccaca    1320
acattttcaa acaacgcaaa gcagtagcag cagcgagaag caagcaagaa gcg atg      1376
                                                                Met
                                                                  1 ggg atg ggg atg agg agg gag agg gac gcg gag gcg gag ctg aac ctg     1424
Gly Met Gly Met Arg Arg Glu Arg Asp Ala Glu Ala Glu Leu Asn Leu
          5                   10                  15 ccg ccg ggg ttc agg ttc cac ccc acg gac gac gag ctg gtg gag cac     1472
Pro Pro Gly Phe Arg Phe His Pro Thr Asp Asp Glu Leu Val Glu His
     20                  25                  30
```

```
tac ctg tgc agg aag gcg gcg ggg cag cgc ctg ccg gtg ccg atc atc    1520
Tyr Leu Cys Arg Lys Ala Ala Gly Gln Arg Leu Pro Val Pro Ile Ile
        35                  40                  45 gcc gag gtg gat ctc tac aag ttc gac ccg tgg gat ctg ccc gag cgc    1568
Ala Glu Val Asp Leu Tyr Lys Phe Asp Pro Trp Asp Leu Pro Glu Arg
50                  55                  60                  65 gcg ctg ttc ggc gcc agg gag tgg tac ttc ttc acc ccg cgg gat cgc    1616
Ala Leu Phe Gly Ala Arg Glu Trp Tyr Phe Phe Thr Pro Arg Asp Arg
                70                  75                  80 aag tat cct aat ggg tca cgc ccc aac cgc gcc gcc ggc aac ggg tac    1664
Lys Tyr Pro Asn Gly Ser Arg Pro Asn Arg Ala Ala Gly Asn Gly Tyr
            85                  90                  95 tgg aag gcc acc ggc gcc gac aag ccc gtc gcg ccg cgg ggg cgc acg    1712
Trp Lys Ala Thr Gly Ala Asp Lys Pro Val Ala Pro Arg Gly Arg Thr
        100                 105                 110 ctt ggg atc aag aag gcg ctc gtg ttc tac gcc ggc aag gcg ccg cga    1760
Leu Gly Ile Lys Lys Ala Leu Val Phe Tyr Ala Gly Lys Ala Pro Arg
    115                 120                 125 ggg gtc aag act gat tgg atc atg cat gag tac cgg ctc gcc gat gct    1808
Gly Val Lys Thr Asp Trp Ile Met His Glu Tyr Arg Leu Ala Asp Ala
130                 135                 140                 145 ggc cgc gcc gcc gcg ggc gcc aag aag gga tct ctc agg gtaagcttag     1857
Gly Arg Ala Ala Ala Gly Ala Lys Lys Gly Ser Leu Arg
                150                 155 ctcagattca tccgaattac tagcaatgat ccttgcttcg atcgaagatt attcggtggg   1917
agtgatgatc gataattgga tcgtggtctg atctgatcgt gtgtgaattg tttgtgcag    1976 ttg gat gat tgg gtg ctg tgt cgg ctg tac aac aag aag aac gag tgg    2024
Leu Asp Asp Trp Val Leu Cys Arg Leu Tyr Asn Lys Lys Asn Glu Trp
160                 165                 170 gag aag atg cag cag ggg aag gag gtg aag gag gag gcg tcc gac atg    2072
Glu Lys Met Gln Gln Gly Lys Glu Val Lys Glu Glu Ala Ser Asp Met
175                 180                 185                 190 gtt acg tcg cag tcg cac tcg cac acc cac tcg tgg ggc gag acg cgc    2120
Val Thr Ser Gln Ser His Ser His Thr His Ser Trp Gly Glu Thr Arg
                195                 200                 205 acg ccg gag tcg gag atc gtg gac aac gac ccc ttc ccg gag ctg gac    2168
Thr Pro Glu Ser Glu Ile Val Asp Asn Asp Pro Phe Pro Glu Leu Asp
            210                 215                 220 tcg ttc ccg gcg ttc cag cct gcg ccg ccg ccg gcg acg gcg atg atg    2216
Ser Phe Pro Ala Phe Gln Pro Ala Pro Pro Pro Ala Thr Ala Met Met
        225                 230                 235 gtg ccc aag aaa gaa tcg atg gac gac gcc acc gcg gcc gcc gcc gcc    2264
Val Pro Lys Lys Glu Ser Met Asp Asp Ala Thr Ala Ala Ala Ala Ala
240                 245                 250 gcc gcc acc atc ccc agg aac aac agc agc ctg ttc gtg gac ctg agc    2312
Ala Ala Thr Ile Pro Arg Asn Asn Ser Ser Leu Phe Val Asp Leu Ser
255                 260                 265                 270 tac gac gat atc cag ggc atg tac agc ggc ctc gac atg ctg ccg ccg    2360
Tyr Asp Asp Ile Gln Gly Met Tyr Ser Gly Leu Asp Met Leu Pro Pro
                275                 280                 285 ggc gac gac ttc tac tcg tcg ctc ttc gcg tcg ccg cgg gtg aag ggg    2408
Gly Asp Asp Phe Tyr Ser Ser Leu Phe Ala Ser Pro Arg Val Lys Gly
            290                 295                 300 acg acg cca cgc gcc ggc gcc ggc atg ggc atg gtc ccg ttc tga        2453
Thr Thr Pro Arg Ala Gly Ala Gly Met Gly Met Val Pro Phe
        305                 310                 315 ggtgacggcg acgcgatcga acaggtggtg atcgatgctg caacgtgtgt aaatatacag   2513
```
cgccggctgg gtcaagagat ggctcgg                                                    2540

<210> SEQ ID NO 2
<211> LENGTH: 316
<212> TYPE: PRT
<213> ORGANISM: Oryza sativa

<400> SEQUENCE: 2

Met Gly Met Gly Met Arg Arg Glu Arg Asp Ala Glu Ala Glu Leu Asn
1               5                   10                  15

Leu Pro Pro Gly Phe Arg Phe His Pro Thr Asp Asp Glu Leu Val Glu
            20                  25                  30

His Tyr Leu Cys Arg Lys Ala Ala Gly Gln Arg Leu Pro Val Pro Ile
        35                  40                  45

Ile Ala Glu Val Asp Leu Tyr Lys Phe Asp Pro Trp Asp Leu Pro Glu
    50                  55                  60

Arg Ala Leu Phe Gly Ala Arg Glu Trp Tyr Phe Phe Thr Pro Arg Asp
65                  70                  75                  80

Arg Lys Tyr Pro Asn Gly Ser Arg Pro Asn Arg Ala Ala Gly Asn Gly
                85                  90                  95

Tyr Trp Lys Ala Thr Gly Ala Asp Lys Pro Val Ala Pro Arg Gly Arg
            100                 105                 110

Thr Leu Gly Ile Lys Lys Ala Leu Val Phe Tyr Ala Gly Lys Ala Pro
        115                 120                 125

Arg Gly Val Lys Thr Asp Trp Ile Met His Glu Tyr Arg Leu Ala Asp
    130                 135                 140

Ala Gly Arg Ala Ala Gly Ala Lys Lys Gly Ser Leu Arg Leu Asp
145                 150                 155                 160

Asp Trp Val Leu Cys Arg Leu Tyr Asn Lys Asn Glu Trp Glu Lys
                165                 170                 175

Met Gln Gln Gly Lys Glu Val Lys Glu Glu Ala Ser Asp Met Val Thr
            180                 185                 190

Ser Gln Ser His Ser His Thr His Ser Trp Gly Glu Thr Arg Thr Pro
        195                 200                 205

Glu Ser Glu Ile Val Asp Asn Asp Pro Phe Pro Glu Leu Asp Ser Phe
    210                 215                 220

Pro Ala Phe Gln Pro Ala Pro Pro Ala Thr Ala Met Met Val Pro
225                 230                 235                 240

Lys Lys Glu Ser Met Asp Asp Ala Thr Ala Ala Ala Ala Ala
                245                 250                 255

Thr Ile Pro Arg Asn Asn Ser Ser Leu Phe Val Asp Leu Ser Tyr Asp
            260                 265                 270

Asp Ile Gln Gly Met Tyr Ser Gly Leu Asp Met Leu Pro Pro Gly Asp
        275                 280                 285

Asp Phe Tyr Ser Ser Leu Phe Ala Ser Pro Arg Val Lys Gly Thr Thr
    290                 295                 300

Pro Arg Ala Gly Ala Gly Met Gly Met Val Pro Phe
305                 310                 315

<210> SEQ ID NO 3
<211> LENGTH: 276
<212> TYPE: PRT
<213> ORGANISM: Oryza sativa

<400> SEQUENCE: 3

```
Met Ala Ala Ala Lys Arg Arg Val Arg Asp Ala Glu Ala Asp Leu Asn
1               5                   10                  15

Leu Pro Pro Gly Phe Arg Phe His Pro Thr Asp Glu Glu Leu Val Ala
            20                  25                  30

His Tyr Leu Cys Pro Arg Ala Ala Gly Arg Ala Ala Pro Val Pro Ile
        35                  40                  45

Ile Ala Glu Leu Asp Leu Tyr Arg His Asp Pro Trp Asp Leu Pro His
50                  55                  60

Arg Ala Leu Phe Gly Arg Arg Glu Trp Tyr Phe Phe Thr Pro Arg Asp
65                  70                  75                  80

Arg Lys Tyr Pro Asn Gly Ser Arg Pro Asn Arg Ala Ala Ala Ser Gly
                85                  90                  95

Tyr Trp Lys Ala Thr Gly Ala Asp Lys Pro Val Leu His Asn Gly Arg
            100                 105                 110

Thr Ala Gly Ile Lys Lys Ala Leu Val Phe Tyr His Gly Lys Pro Pro
        115                 120                 125

Arg Gly Val Lys Thr Glu Trp Ile Met His Glu Tyr Arg Leu Ala Lys
130                 135                 140

Lys Gly Gly Ala Ala Ala Ala Gly Ala Gly Ala Leu Arg Leu Asp
145                 150                 155                 160

Asp Trp Val Leu Cys Arg Leu Tyr Asn Lys Lys Asn Glu Trp Glu Lys
                165                 170                 175

Met Gln Ser Arg Lys Glu Glu Glu Ala Met Ala Ala Gln Ser
            180                 185                 190

Trp Gly Glu Thr Arg Thr Pro Glu Ser Glu Val Val Asp Ser Asp Ala
            195                 200                 205

Phe Pro Glu Met Asp Tyr Ser Leu Pro Ala Ala Ser Phe Asp Ala
        210                 215                 220

Leu Leu Pro Lys Glu Glu Ala Arg Asp Asp Asp Trp Leu Met Gly Met
225                 230                 235                 240

Ser Leu Asp Asp Leu Gln Gly Leu Gly Ser Leu Leu Gln Ala Asp Asp
                245                 250                 255

Leu Ser Met Leu Ala Pro Pro Ala Ala Lys Thr Glu Pro Leu Gly
            260                 265                 270

Ala Pro Phe Phe
        275

<210> SEQ ID NO 4
<211> LENGTH: 316
<212> TYPE: PRT
<213> ORGANISM: Oryza sativa

<400> SEQUENCE: 4

Met Ala Ala Ala Val Gly Gly Ser Gly Arg Arg Asp Ala Glu Ala Glu
1               5                   10                  15

Leu Asn Leu Pro Pro Gly Phe Arg Phe His Pro Thr Asp Glu Glu Leu
            20                  25                  30

Val Val His Tyr Leu Cys Arg Lys Val Ala Arg Gln Pro Leu Pro Val
        35                  40                  45

Pro Ile Ile Ala Glu Val Asp Leu Tyr Lys Leu Asp Pro Trp Asp Leu
50                  55                  60

Pro Glu Lys Ala Leu Phe Gly Arg Lys Glu Trp Tyr Phe Phe Thr Pro
65                  70                  75                  80

Arg Asp Arg Lys Tyr Pro Asn Gly Ser Arg Pro Asn Arg Ala Ala Gly
                85                  90                  95
```

```
Arg Gly Tyr Trp Lys Ala Thr Gly Ala Asp Lys Pro Val Ala Pro Lys
            100                 105                 110

Gly Ser Ala Arg Thr Val Gly Ile Lys Lys Ala Leu Val Phe Tyr Ser
        115                 120                 125

Gly Lys Ala Pro Arg Gly Val Lys Thr Asp Trp Ile Met His Glu Tyr
    130                 135                 140

Arg Leu Ala Asp Ala Asp Arg Ala Pro Gly Gly Lys Lys Gly Ser Gln
145                 150                 155                 160

Lys Leu Asp Glu Trp Val Leu Cys Arg Leu Tyr Asn Lys Lys Asn Asn
                165                 170                 175

Trp Glu Lys Val Lys Leu Glu Gln Gln Asp Val Ala Ser Val Ala Ala
            180                 185                 190

Ala Ala Pro Arg Asn His His His Gln Asn Gly Glu Val Met Asp Ala
        195                 200                 205

Ala Ala Ala Asp Thr Met Ser Asp Ser Phe Gln Thr His Asp Ser Asp
    210                 215                 220

Ile Asp Asn Ala Ser Ala Gly Leu Arg His Gly Gly Cys Gly Gly Gly
225                 230                 235                 240

Gly Phe Gly Asp Val Ala Pro Pro Arg Asn Gly Phe Val Thr Val Lys
                245                 250                 255

Glu Asp Asn Asp Trp Phe Thr Gly Leu Asn Phe Asp Glu Leu Gln Pro
            260                 265                 270

Pro Tyr Met Met Asn Leu Gln His Met Gln Met Gln Met Val Asn Pro
        275                 280                 285

Ala Ala Pro Gly His Asp Gly Gly Tyr Leu Gln Ser Ile Ser Ser Pro
    290                 295                 300

Gln Met Lys Met Trp Gln Thr Ile Leu Pro Pro Phe
305                 310                 315

<210> SEQ ID NO 5
<211> LENGTH: 303
<212> TYPE: PRT
<213> ORGANISM: Oryza sativa

<400> SEQUENCE: 5

Met Ser Gly Gly Gln Asp Leu Gln Leu Pro Pro Gly Phe Arg Phe His
1               5                   10                  15

Pro Thr Asp Glu Glu Leu Val Met His Tyr Leu Cys Arg Arg Cys Ala
            20                  25                  30

Gly Leu Pro Ile Ala Val Pro Ile Ile Ala Glu Ile Asp Leu Tyr Lys
        35                  40                  45

Phe Asp Pro Trp Gln Leu Pro Arg Met Ala Leu Tyr Gly Glu Lys Glu
    50                  55                  60

Trp Tyr Phe Phe Ser Pro Arg Asp Arg Lys Tyr Pro Asn Gly Ser Arg
65                  70                  75                  80

Pro Asn Arg Ala Ala Gly Ser Gly Tyr Trp Lys Ala Thr Gly Ala Asp
                85                  90                  95

Lys Pro Val Gly Ser Pro Lys Pro Val Ala Ile Lys Lys Ala Leu Val
            100                 105                 110

Phe Tyr Ala Gly Lys Ala Pro Lys Gly Glu Lys Thr Asn Trp Ile Met
        115                 120                 125

His Glu Tyr Arg Leu Ala Asp Val Asp Arg Ser Ala Arg Lys Lys Asn
    130                 135                 140
```

```
Ser Leu Arg Leu Asp Asp Trp Val Leu Cys Arg Ile Tyr Asn Lys Lys
145                 150                 155                 160

Gly Gly Leu Glu Lys Pro Pro Ala Ala Val Ala Ala Ala Gly Met
            165                 170                 175

Val Ser Ser Gly Gly Val Gln Arg Lys Pro Met Val Gly Val Asn
        180                 185                 190

Ala Ala Val Ser Ser Pro Pro Glu Gln Lys Pro Val Val Ala Gly Pro
            195                 200                 205

Ala Phe Pro Asp Leu Ala Ala Tyr Tyr Asp Arg Pro Ser Asp Ser Met
        210                 215                 220

Pro Arg Leu His Ala Asp Ser Ser Cys Ser Glu Gln Val Leu Ser Pro
225                 230                 235                 240

Glu Phe Ala Cys Glu Val Gln Ser Gln Pro Lys Ile Ser Glu Trp Glu
                245                 250                 255

Arg Thr Phe Ala Thr Val Gly Pro Ile Asn Pro Ala Ala Ser Ile Leu
                260                 265                 270

Asp Pro Ala Gly Ser Gly Gly Leu Gly Gly Leu Gly Gly Gly Ser
            275                 280                 285

Asp Pro Leu Leu Gln Asp Ile Leu Met Tyr Trp Gly Lys Pro Phe
        290                 295                 300

<210> SEQ ID NO 6
<211> LENGTH: 297
<212> TYPE: PRT
<213> ORGANISM: Arabidopsis thaliana

<400> SEQUENCE: 6

Met Gly Val Arg Glu Lys Asp Pro Leu Ala Gln Leu Ser Leu Pro Pro
1               5                   10                  15

Gly Phe Arg Phe Tyr Pro Thr Asp Glu Glu Leu Leu Val Gln Tyr Leu
            20                  25                  30

Cys Arg Lys Val Ala Gly Tyr His Phe Ser Leu Gln Val Ile Gly Asp
        35                  40                  45

Ile Asp Leu Tyr Lys Phe Asp Pro Trp Asp Leu Pro Ser Lys Ala Leu
50                  55                  60

Phe Gly Glu Lys Glu Trp Tyr Phe Phe Ser Pro Arg Asp Arg Lys Tyr
65                  70                  75                  80

Pro Asn Gly Ser Arg Pro Asn Arg Val Ala Gly Ser Gly Tyr Trp Lys
                85                  90                  95

Ala Thr Gly Thr Asp Lys Ile Ile Thr Ala Asp Gly Arg Arg Val Gly
            100                 105                 110

Ile Lys Lys Ala Leu Val Phe Tyr Ala Gly Lys Ala Pro Lys Gly Thr
        115                 120                 125

Lys Thr Asn Trp Ile Met His Glu Tyr Arg Leu Ile Glu His Ser Arg
130                 135                 140

Ser His Gly Ser Ser Lys Leu Asp Asp Trp Val Leu Cys Arg Ile Tyr
145                 150                 155                 160

Lys Lys Thr Ser Gly Ser Gln Arg Gln Ala Val Thr Pro Val Gln Ala
                165                 170                 175

Cys Arg Glu Glu His Ser Thr Asn Gly Ser Ser Ser Ser Ser Ser
            180                 185                 190

Gln Leu Asp Asp Val Leu Asp Ser Phe Pro Glu Ile Lys Asp Gln Ser
        195                 200                 205

Phe Asn Leu Pro Arg Met Asn Ser Leu Arg Thr Ile Leu Asn Gly Asn
210                 215                 220
```

```
Phe Asp Trp Ala Ser Leu Ala Gly Leu Asn Pro Ile Pro Glu Leu Ala
225                 230                 235                 240

Pro Thr Asn Gly Leu Pro Ser Tyr Gly Gly Tyr Asp Ala Phe Arg Ala
            245                 250                 255

Ala Glu Gly Glu Ala Glu Ser Gly His Val Asn Arg Gln Gln Asn Ser
        260                 265                 270

Ser Gly Leu Thr Gln Ser Phe Gly Tyr Ser Ser Gly Phe Gly Val
    275                 280                 285

Ser Gly Gln Thr Phe Glu Phe Arg Gln
    290                 295

<210> SEQ ID NO 7
<211> LENGTH: 324
<212> TYPE: PRT
<213> ORGANISM: Arabidopsis thaliana

<400> SEQUENCE: 7

Met Glu Thr Glu Glu Met Lys Glu Ser Ser Ile Ser Met Val Glu
1               5                   10                  15

Ala Lys Leu Pro Pro Gly Phe Arg Phe His Pro Lys Asp Asp Glu Leu
            20                  25                  30

Val Cys Asp Tyr Leu Met Arg Arg Ser Leu His Asn Asn His Arg Pro
        35                  40                  45

Pro Leu Val Leu Ile Gln Val Asp Leu Asn Lys Cys Glu Pro Trp Asp
    50                  55                  60

Ile Pro Lys Met Ala Cys Val Gly Gly Lys Asp Trp Tyr Phe Tyr Ser
65                  70                  75                  80

Gln Arg Asp Arg Lys Tyr Ala Thr Gly Leu Arg Thr Asn Arg Ala Thr
                85                  90                  95

Ala Thr Gly Tyr Trp Lys Ala Thr Gly Lys Asp Arg Thr Ile Leu Arg
            100                 105                 110

Lys Gly Lys Leu Val Gly Met Arg Lys Thr Leu Val Phe Tyr Gln Gly
        115                 120                 125

Arg Ala Pro Arg Gly Arg Lys Thr Asp Trp Val Met His Glu Phe Arg
    130                 135                 140

Leu Gln Gly Ser His His Pro Asn His Ser Leu Ser Ser Pro Lys
145                 150                 155                 160

Glu Asp Trp Val Leu Cys Arg Val Phe His Lys Asn Thr Glu Gly Val
                165                 170                 175

Ile Cys Arg Asp Asn Met Gly Ser Cys Phe Asp Glu Thr Ala Ser Ala
            180                 185                 190

Ser Leu Pro Pro Leu Met Asp Pro Tyr Ile Asn Phe Asp Gln Glu Pro
        195                 200                 205

Ser Ser Tyr Leu Ser Asp Asp His His Tyr Ile Ile Asn Glu His Val
    210                 215                 220

Pro Cys Phe Ser Asn Leu Ser Gln Asn Gln Thr Leu Asn Ser Asn Leu
225                 230                 235                 240

Thr Asn Ser Val Ser Glu Leu Lys Ile Pro Cys Lys Asn Pro Asn Pro
                245                 250                 255

Leu Phe Thr Gly Gly Ser Ala Ser Ala Thr Leu Thr Gly Leu Asp Ser
            260                 265                 270

Phe Cys Ser Ser Asp Gln Met Val Leu Arg Ala Leu Leu Ser Gln Leu
        275                 280                 285
```

```
Thr Lys Ile Asp Gly Ser Leu Gly Pro Lys Glu Ser Gln Ser Tyr Gly
    290                 295                 300

Glu Gly Ser Ser Glu Ser Leu Leu Thr Asp Ile Gly Ile Pro Ser Thr
305                 310                 315                 320

Val Trp Asn Cys

<210> SEQ ID NO 8
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 8
cagaattcaa agcaacagtg gagagaaaac                                    30

<210> SEQ ID NO 9
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 9
taggatcccc gagccatctc ttgac                                         25

<210> SEQ ID NO 10
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 10
taggtaccag aagcaagcaa gaagcgat                                      28

<210> SEQ ID NO 11
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 11
agaagcaagc aagaagcgat                                               20

<210> SEQ ID NO 12
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 12
ccgagccatc tcttgac                                                  17

<210> SEQ ID NO 13
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 13
tccgacacag cacccaatca tc                                            22
```

<210> SEQ ID NO 14
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 14
tatcgtcgta gctcaggtcc a                                              21

<210> SEQ ID NO 15
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 15
ctttcttggg caccatcat                                                 19

<210> SEQ ID NO 16
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 16
acgggaaggg gtcgttgtcc a                                              21

<210> SEQ ID NO 17
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 17
ctgtacaaca agaagaacg                                                 19

<210> SEQ ID NO 18
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 18
ggggacaagt ttgtacaaaa aagcaggct                                      29

<210> SEQ ID NO 19
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 19
ggggaccact ttgtacaaga aagctgggt                                      29

<210> SEQ ID NO 20
<211> LENGTH: 29
<212> TYPE: DNA
<213> ORGANISM: Artificial Sequence
<220> FEATURE:

```
-continued

<223> OTHER INFORMATION: Synthetic polynucleotide

<400> SEQUENCE: 20
caaagcttgc gtgacccatt aggatactt                                              29
```